US012239369B2

(12) United States Patent
Mok

(10) Patent No.: US 12,239,369 B2
(45) Date of Patent: Mar. 4, 2025

(54) METHODS AND SYSTEMS FOR AN APPARATUS FOR PRECISE TISSUE PHOTOMODIFICATION

(71) Applicant: Allure Medical Spa PLLC, Shelby Township, MI (US)

(72) Inventor: Charles Mok, Shelby Township, MI (US)

(73) Assignee: Allure Medical Spa, P.L.L.C, Shelby Township, MI (US)

( * ) Notice: Subject to any disclaimer, the term of this patent is extended or adjusted under 35 U.S.C. 154(b) by 0 days.

(21) Appl. No.: 18/219,857

(22) Filed: Jul. 10, 2023

(65) Prior Publication Data
US 2025/0017651 A1 Jan. 16, 2025

(51) Int. Cl.
A61B 18/20 (2006.01)
A61B 18/00 (2006.01)

(52) U.S. Cl.
CPC ........ A61B 18/203 (2013.01); A61B 2018/00452 (2013.01); A61B 2018/00773 (2013.01)

(58) Field of Classification Search
CPC ........ A61B 18/203; A61B 2018/00452; A61B 2018/00773
See application file for complete search history.

(56) References Cited

U.S. PATENT DOCUMENTS

| 2008/0033410 | A1* | 2/2008 | Rastegar | A61B 34/30 |
| | | | | 606/9 |
| 2018/0093103 | A1* | 4/2018 | Pryor | G16Z 99/00 |
| 2022/0401750 | A1* | 12/2022 | Daly | A61N 5/0616 |
| 2023/0225813 | A1* | 7/2023 | Roh | A61B 34/10 |
| | | | | 607/89 |
| 2023/0404667 | A1* | 12/2023 | Herzog | A61B 34/37 |

FOREIGN PATENT DOCUMENTS

WO WO-2021130052 A1 * 7/2021 ........... A61B 18/203

* cited by examiner

Primary Examiner — Gary Jackson
Assistant Examiner — Sebastian X Lukjan
(74) Attorney, Agent, or Firm — Caldwell Intellectual Property Law

(57) ABSTRACT

An apparatus for precise tissue photo modification, the apparatus comprising an input device; a light-emitting device for use in precise tissue destruction, comprising one or more light settings, the one or more settings having at least a power density setting, a processor, and a memory communicatively connected to the processor. The memory contains instructions configuring the processor to receive a plurality of user data from the input device, wherein the plurality of user data from the input device comprises at least a template datum, generate a plurality of light emission parameters for the one or more light settings as a function of the plurality of user data, and modify a user interface as a function of the plurality of light emission parameters, wherein the processor is configured to transmit a light command as a function of user input with the user interface.

18 Claims, 8 Drawing Sheets

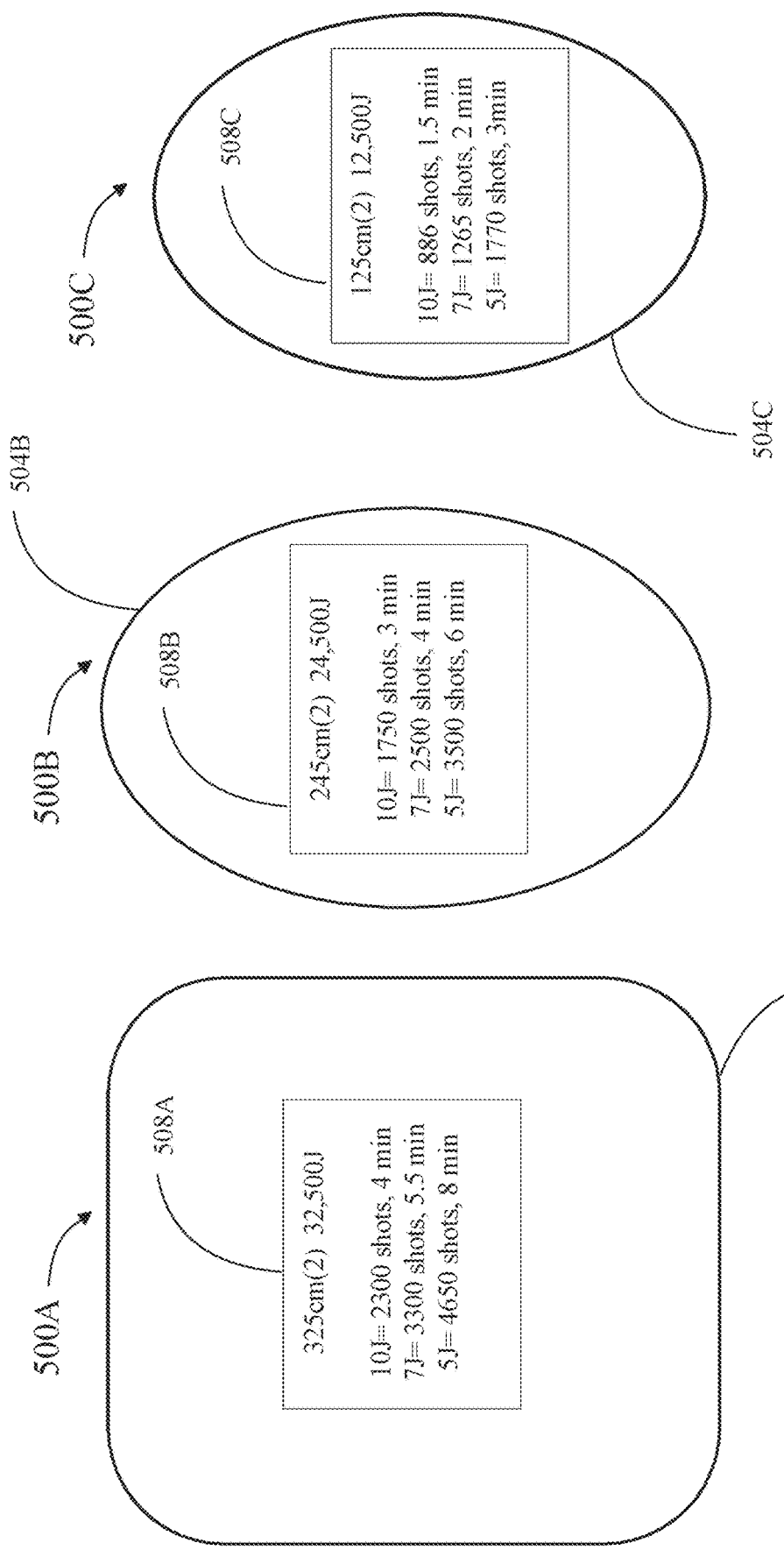

US 12,239,369 B2

METHODS AND SYSTEMS FOR AN APPARATUS FOR PRECISE TISSUE PHOTOMODIFICATION

FIELD OF THE INVENTION

The present invention generally relates to the field of lasers. In particular, the present invention is directed to precise tissue destruction such as laser hair removal or tattoo removal using laser light.

BACKGROUND

Laser hair removal is the process in which light destroys hair molecules using heat. During laser removal, light is emitted onto the surface of human tissue and absorbed primarily by hair follicles present on the surface. The absorbed light causes the hair follicle to heat up and ultimately destroy the stem cells within the hair follicle. The light achieves this process by emitting a wavelength of light that is primarily absorbed by darker materials, such as the melanin in hair, while reflecting off lighter materials such as skin. Current approaches to administration of the light to subject tissue are too inexact.

SUMMARY OF THE DISCLOSURE

In an aspect an apparatus for precise tissue photo modification is illustrated. The apparatus includes an input device and a light-emitting device for use in precise tissue destruction comprising one or more settings. The one or more settings on the light-emitting emitting device contains at least a power density setting. The apparatus further includes a processor and a memory communicatively connected to the processor. The memory contains instructions configuring the processor to receive a plurality of user data from the input device. The plurality of user data retrieved from the input device comprises at least a template datum. The memory further contains instructions to generate a plurality of light emission parameters for the one or more settings on the light-emitting device as a function of the plurality of user data. The memory further contains instructions to modify a user interface as a function of the plurality of light emission parameters, wherein the processor is configured to transmit a light command as a function of user input with the user interface.

In another aspect a method for precise tissue photo modification is illustrated. The method includes recording by an input device a plurality of user data, the plurality of user data having at least a template datum. Further, the method includes generating, by a memory communicatively connected to at least a processor, a plurality of light emission parameters as a function of the plurality of user data and inputting the plurality of light emission parameters into one or more settings of a light-emitting device. The method further includes modifying by the memory communicatively connected to the at least a processor, a user interface as a function of the plurality of light emission parameters. The method further includes guiding the light-emitting device over a surface of a skin wherein a laser light having a wavelength is absorbed by the skin, destroying a selection portion of tissue on the skin.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 5A-E are exemplary embodiments of templates according to the subject disclosure;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for precise tissue photo modification using a light-emitting device. In some embodiments, the system comprises an input device, a light-emitting device, a computing device, and a user display. In some embodiments, the system may further comprise an automated arm.

Figure 1:
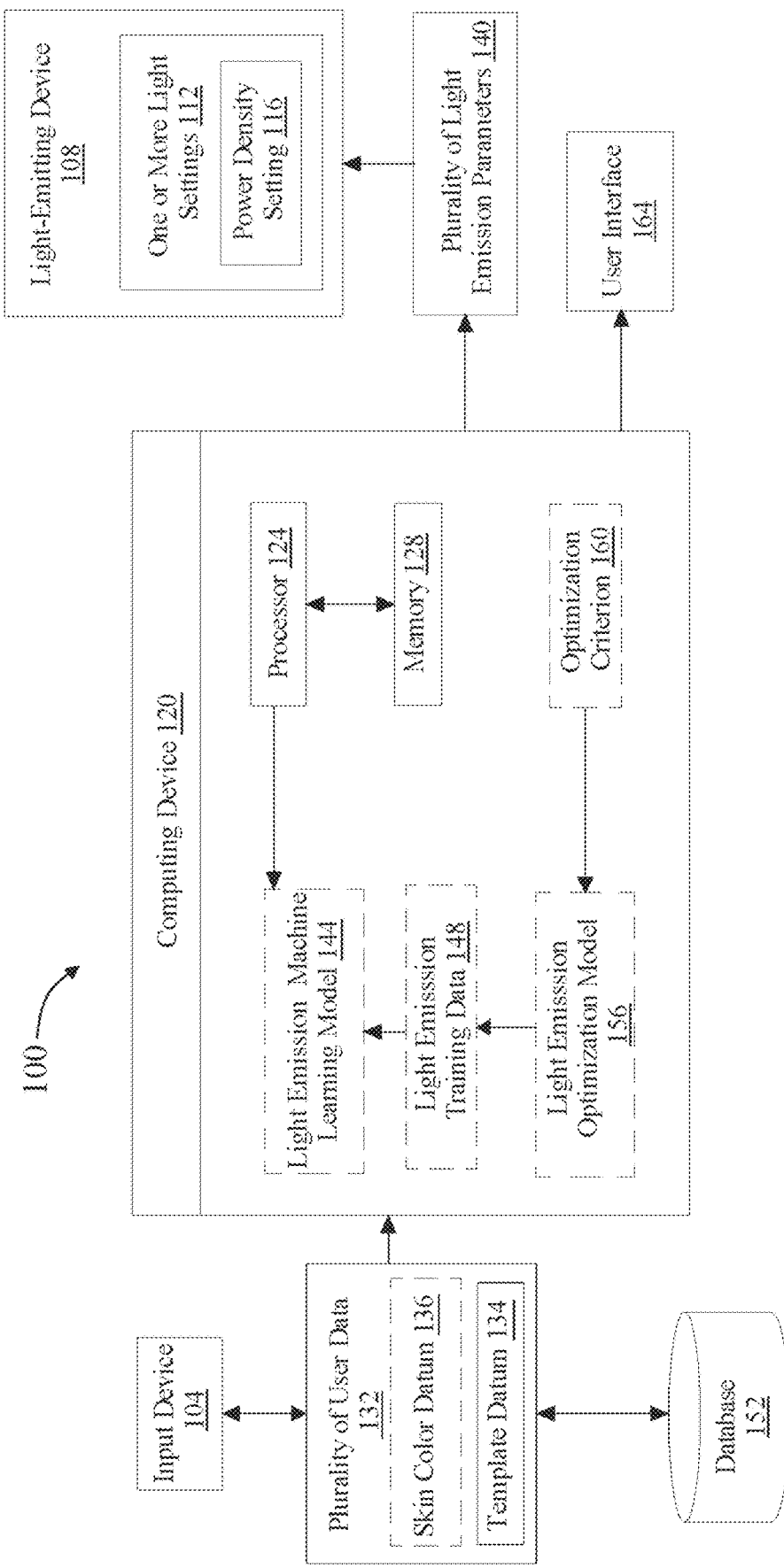
FIG. 1 is a block diagram of an apparatus according to an embodiment of the invention.

Referring now to FIG. 1, an exemplary embodiment of an apparatus 100 for precise tissue photo modification is illustrated. Still referring to FIG. 1, in one embodiment, the apparatus 100 includes an input device 104. "Input device" as used in this disclosure refers any sort of input device that inputs data into a computing device. For example, input device 104 may refer to a user generated input method or a may refer to a computer-generated input method. Examples of input device 104 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device may further include a plurality of sensors. Input device 104 may further include a photo electric sensor having three color filters corresponding to the red, green, and blue color space. The photoelectric sensor outputs data in the form of voltages corresponding to a color. Additionally, or alternatively, input device 104 may include a video capture device. The video capture device may record still or moving images in the form of video and transmit the images to the computing device 120. As described below, computing device 120 may then determine objects and colors within the still or moving images using machine learning algorithms.

Continuing in FIG. 1, apparatus 100 includes a light-emitting device 108. "Light-emitting device" as used in this disclosure is a device that emits a light capable of tissue photo modification. "Tissue photo modification" as used in this disclosure is the process of tissue destruction through the selection of specific chromophores such as the melanin in hair or the ink particles in tattoo pigments. Lights capable of photo modification are lights that can target and destroy specific chromophores, darker skin tissue, or tattoo pigments on the patient's skin. For example, lights capable of heating and destroying specific chromophores may include lasers such as ruby laser systems, alexandrite laser systems, diode laser systems or neodymium-doped yttrium aluminum garnet laser systems. Light-emitting device 108 may also include non-laser intense pulsed light ("IPL") devices that are capable of high output bursts of a broad spectrum of light. For example, the light-emitting device 108 may use a Xenon flash lamp to destroy specific chromophores while leaving surrounding tissue undamaged. Light-emitting device 108 may have varying wavelengths of light ranging from 400 nanometers to 1200 nanometers (nm). Light-emitting device may include a ruby laser when a shorter wavelength is desired. A ruby laser typically has a wavelength of 694 nm and is desired when a user has lighter skin and thinner hair. Light-emitting device may also include an alexandrite hair removal laser. An alexandrite hair removal laser typically has a wavelength of 755 nm and is used when a higher wavelength is desired as compared to a ruby laser. Light-emitting device may further contain a diode laser. A diode laser operates in the range of 800 nm and may be used for generally darker skin types and can be used for thicker hair as well. Light-emitting device may also contain an ND: YAG laser. An ND: YAG laser is a neodymium-doped yttrium aluminum garnet laser. ND: YAG lasers operate in the range of 1064 nm and is desired in individuals with darker skin types. ND: YAG lasers may also be used to reverse sun damage and for tattoo removal. Varying wavelengths of light allow the light-emitting device 108 to attack specific chromophores while reflecting off the surrounding tissue. For example, a patient with melanin rich skin may benefit from a higher wavelength light-emitting device 108. Higher wavelengths attack the dark pigments in dark hair while sparing lighter epidermal pigment. Light-emitting device may also include intense pulsed light (IPL) as described above. IPL devices typically output a broad spectrum of light generally within a wavelength range from 400 nm to 1200 nm. IPL. Filters can be used to block shorter wavelengths and thereby control the wavelength of the IPL device as will be discussed below.

Still referring to FIG. 1, light-emitting device 108 may include one or more optical elements for focusing, collimating, and/or transmitting light emitted by light source. One or more optical elements may include a focal optical suite, which may bend light to converge to a real and/or virtual focal point. Focal optical suite may be reflective, diffractive, adaptive, and/or refractive; for instance, and without limitation, focal optical suite may include two or more lenses spaced apart, where spacing between lenses may be varied to modify a focal length of transmitted light. Dispersal and/or focus of transmitted light may be controlled using electronically focused lens and/or reflective assembly, where adjustment of distances or alignment between lenses and/or mirrors may be electrically or mechanically actuated. Intensity or temporal composition of transmitted light may be variable as well, where variation may be modified using varied voltage levels, electrical current levels, waveforms, multiple pulses, duty cycles, pulse widths, passive or active optical elements, such as Q-switches, acoustical optical tunable filters (AOTF), acousto-optical modulators, electro-optical modulators, and/or spatial light modulators (SLM). Electrical voltage and current levels, and durations to light source may be regulated analog or digitally by output of a logic circuit and/or processor 124 to a digital to analog converter, an on/off cycle to a transistor such as a power field-effect transistor, pulse width modulation provided natively by a processor, or the like.

Still in FIG. 1, light-emitting device 108 contains one or more light settings 112. One or more light settings 112 includes a power density setting 116. "Power density setting" as defined in this disclosure refers to the given number of photons directed to a concentrated area. The power density setting 116 (Sometimes known as irradiance) is calculated as a function of a power and a spot size of the light-emitting device 108. Power of the light-emitting device 108 is power that is delivered through the light emitted from the light-emitting device 108. Power is quantified in watts or joules per second. Spot size refers to the area in which the light is delivered. Spot size is quantified in square centimeter. Power density setting 116 is quantified in watts per square centimeter. A power density with a larger output may be achieved by either increasing the power output or decreasing the spot size. Power density with a larger output may be desired in situations where more photons would be needed for a desired target. The power density setting 116 may be calculated either through input device 104 as described above or through a dial on the light-emitting device 108. Power density setting 116 may also be calculated by the computing device 120 as will be described below. The data correlating to a specific power density setting 116 may be quantified as a power density datum.

One or more light settings 112 of light-emitting device 108 may also contain a wavelength setting. Wavelength refers to the wavelength of light that is produced by the light-emitting device 108 and is quantified in nanometers. Wavelength may be important in precise tissue photo modification as the wavelength determines the chromophore that should be targeted by the light. Shorter wavelengths generally have lower absorption rates and therefore are useful in patients who lack melanin rich skin. Longer wavelengths are preferred in patients with melanin rich skin as the longer wavelengths can penetrate past the epidermis and attack only the hair or ink follicles while leaving the surrounding skin unharmed. A particular wavelength may be chosen based on the need for the light or laser to be absorbed by the hair follicle, specific chromophore or skin pigment that is being targeted. Wavelength may be varied using a tunable laser. "Tunable laser" as described in this disclosure is a laser whose wavelength may be altered within a defined range. For example, an ND: YAG laser having a wavelength of 1064 nanometers may be tuned to a wavelength of 1052 nm or to a wavelength of 1319 nm. Lasers may be tuned using single line tuning. Single line tuning refers to the placement of optical elements into a laser's optical cavity in order to tune the output of a laser to a desired wavelength. Similarly, lasers may be tuned using multi-line tuning. Multi-line tuning refers to suppression of a laser's principal wavelength output in order to focus on weaker wavelengths that are emitted from a laser. For example, an ND: YAG laser may have weaker wavelengths that can be focused when its principal output at 1,064 nm is suppressed. Additionally, or alternatively, light-emitting device 108 may have multiple lasing mediums such that a desired wavelength may be chosen from a wide variety of lasing mediums. "Lasing medium" as described in this disclosure refers to the source of the optical gain within a laser. For example, a ruby laser may use ruby crystals as the lasing medium. The ruby crystals are excited by an energy source such that light is released within a specific wavelength. Additionally, or alternatively, intense pulsed light may be used to vary wavelength of light-emitting device 108. for example, an IPL device may utilize a wavelength filter cutoff of 630 nm such that wavelengths below 630 nm are blocked out. As a result, a wavelength of 630 nm to 1200 nm can be utilized for users with darker skin. Wavelength setting of the light-emitting device 108 may be controlled through a dial or through input device 104 as described above. The wavelength setting may also be controlled by the computing device 120 as will be described below. The data correlating to a specific wavelength setting may be quantified as wavelength datum.

One or more light settings 112 of light-emitting device 108 may also contain a pulse width setting. A "pulse width" (sometimes also known as "pulse length") as defined in this disclosure is the exposure time of the light-emitting device 108 on the surface of a patient's skin. Pulse width is quantified in seconds. The duration of the pulse width may be dependent on the skin color of a patient, the ink color on the patient's skin or the thickness of a patient's hair. For example, a patient with thinner hair would require a smaller pulse width as the thinner hair can heat up quickly, whereas a patient with thicker hair would require a higher pulse width as thicker hair takes longer to heat up. Pulse width for laser hair removal may range from between 3 milliseconds up to 100 milliseconds. However, pulse width for tattoo pigment removal may have smaller pulse widths in the ranges of nanoseconds and picoseconds. Pulse width setting may be used to increase or decrease the pulse width in the light-emitting device 108. The data correlating to a specific pulse width setting may be quantified as a pulse width datum.

Pulse width may be varied, without limitation, using Q-switching. "Q-switching" as described in this disclosure refers to the technique in which a laser can output light in short durations or pulses. Unlike common lasers which emit continuous light, Q-switching allows light to be emitted in short pulses. Q-Switching may be beneficial in laser hair removal in order to control the pulse width of the light-emitting device 108. Q-switching may be achieved by placing a q-switch within the light-emitting device wherein the q-switch is set to prevent feedback of light until a maximum energy level is achieved. Once a maximum energy level is achieved, the q-switch device allows feedback of light and as a result a short pulse of light is emitted. Q-switching may be used to control pulse widths or to control the power density of the laser. Pulse width may also be varied through a power duty cycle. A "power duty cycle" as described in this disclosure is a cycle in which power is delivered for a specified period. Power duty cycle may be used to control the power output of the laser for brief periods of time such that the pulse width can be controlled. Pulse width may be varied using similar techniques as well such as shuttering wherein laser beams are blocked by inserting or removing an absorbing or reflecting blade. Pulse width may further be varied using similar techniques in which light is emitted for brief periods.

The pulse width together with the power density described above create the energy density (sometimes known as "fluence"). "Energy density" as described in this disclosure is the total amount of energy delivered per unit area in joules per square centimeter. The energy density is calculated by multiplying the power density by the width. Energy density may range from 3 joules per square centimeter up to 120 joules per square centimeter. However, it is to be noted that the energy delivered may be delivered over several intervals and not immediately in one passing.

One or more light settings 112 of light-emitting device 108 may further contain a cooling setting. "Cooling setting" as defined in this disclosure is any form of cooling that may occur to reduce the temperature on a surface. For example, light-emitting device 108 may contain a fan that blows air onto the heated surface, thereby dissipating any heat. Further light-emitting device 108 may contain the cooling setting using air conditioned or cryogenic air. The dissipation of heat from the surface of patient's skin may aid in the minimization of burns and other damages that occur to the skin because of the light-emitting device 108. Cooling setting may be controlled through a dial, push button or input device 104 described above. Cooling setting may also be controlled by the computing device 120 described below. The data correlating to a specific cooling setting may be quantified as cooling datum.

Light-emitting device 108 may contain a handle such that the user can properly grip the light-emitting device 108 in their hand. Light-emitting device 108 may further contain a push button located on a surface of the light-emitting device 108. The pressing of the push button may activate or focus the light that is emitted from the light-emitting device 108.

Still referring to FIG. 1, apparatus 100 includes the computing device 120. Computing device 120 includes a processor 124 communicatively connected to a memory 128 wherein the memory 128 contains instructions configuring processor 124 to receive a plurality of user data 132 from input device 104. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device 120. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, Computing device 120 may include any computing device 120 as described in this disclosure, including without limitation a microcontroller, microprocessor, digital signal processor (DSP) and/or system on a chip (SoC) as described in this disclosure. Computing device 120 may include, be included in, and/or communicate with a mobile device such as a mobile telephone or smartphone. Computing device 120 may include a single computing device 120 operating independently or may include two or more computing device 120 operating in concert, in parallel, sequentially or the like; two or more computing devices 120 may be included together in a single computing device 120 or in two or more computing devices 120. Computing device 120 may interface or communicate with one or more additional devices as described below in further detail via a network interface device. Network interface device may be utilized for connecting computing device 120 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 120. Computing device 120 may include but is not limited to, for example, a computing device 120 or cluster of computing devices in a first location and a second computing device 120 or cluster of computing devices in a second location. Computing device 120 may include one or more computing devices dedicated to data storage, security, distribution of traffic for load balancing, and the like. Computing device 120 may distribute one or more computing tasks as described below across a plurality of computing devices of computing device 120, which may operate in parallel, in series, redundantly, or in any other manner used for distribution of tasks or memory 128 between computing devices. Computing device 120 may be implemented using a "shared nothing" architecture in which data is cached at the worker, in an embodiment, this may enable scalability of apparatus 100 and/or computing device 120.

With continued reference to FIG. 1, computing device 120 may be designed and/or configured to perform any method, method step, or sequence of method steps in any embodiment described in this disclosure, in any order and with any degree of repetition. For instance, computing device 120 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 120 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, additionally, computing device 120 may perform determinations, classification, and/or analysis steps, methods, processes, or the like as described in this disclosure using machine learning processes. A "machine learning process," as used in this disclosure, is a process that automatedly uses a body of data known as "training data" and/or a "training set" (described further below) to generate an algorithm that will be performed by a computing device/module to produce outputs given data provided as inputs; this is in contrast to a non-machine learning software program where the commands to be executed are determined in advance by a user and written in a programming language. Machine-learning process may utilize supervised, unsupervised, lazy-learning processes and/or neural networks, described further below.

Figure 5E:
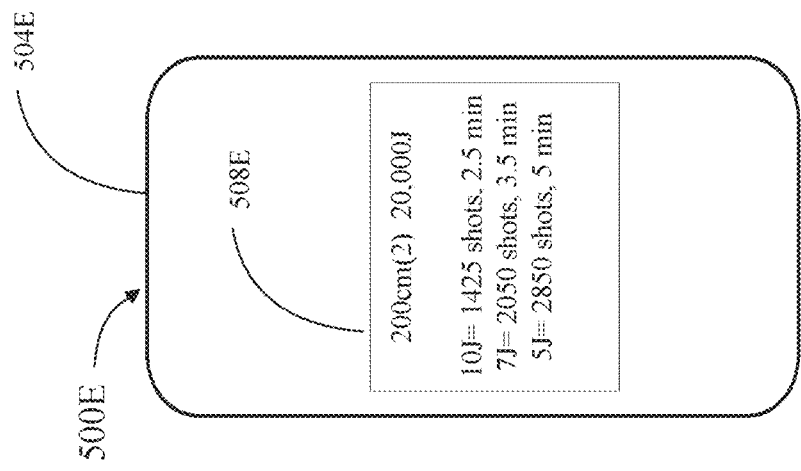
Figure 5D:
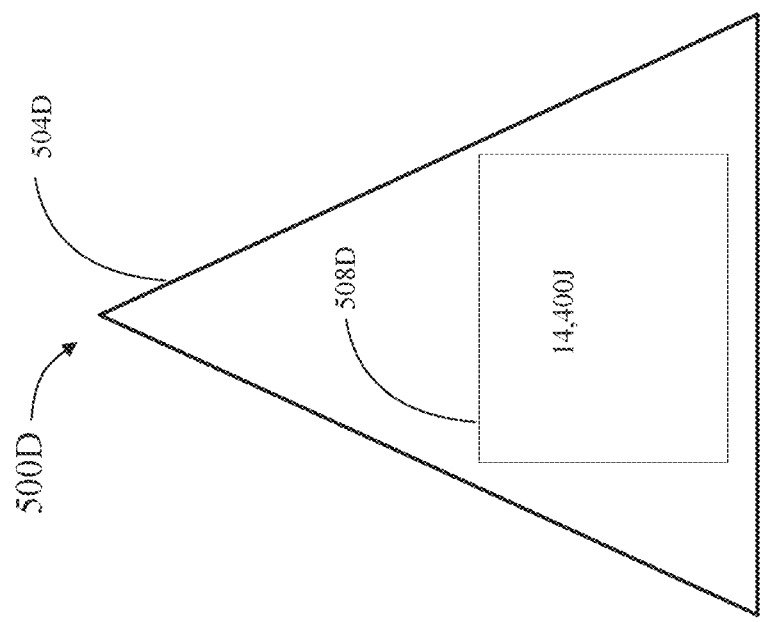

With continued reference to FIG. 1, computing device 120 may be configured to receive the plurality of user data 132 from input device 104. Plurality of user data 132 includes at least a template datum 134. Plurality of user data 132 may further include at least a skin color datum 136. Template datum 134 may be received by a template. A "template" for the purposes of this disclosure is a device configured to generate and/or receive a predetermined set of coordinates for light emitting device 108 to be guided on. For example, template may include a stencil used to draw a path and/or an outline or a particular area to be guided on. In some cases, template may include a component having predefined boundaries and predefined parameters wherein a stencil or a similar physical or digital marking tool may be used to draw the boundary on a user's skin. In this instance. Template may provide computing device with the predefined parameters by providing an area on a user's skin for photo modification and the necessary parameters with respect to the skin area. For example, template may include a component having a predefined size wherein the component is placed on a surface of a user's skin and traced wherein computing device 120 is configured to determine the boundaries of the user's skin based on the trace and provide photo modification to the traced area. Template may be described in further details below such as in FIG. 5. Template may further include a camera configured to receive images relating to a particular path to be guided on. In some cases, template may include an input device as described in this disclosure. In some cases, template may include any device capable of generating boundaries and/or constraints for a light emitting device 108 for use during photo modification. In some cases, template may include a virtual device such a virtual stencil wherein a user may use virtual device to draw and/or map out a particular area for light emitting device 108 to be guided on. In some cases, template may receive data indicating to a user and/or computing device 120 that light emitting device 108 should be guided over a particular area of a user's body. In some cases, template may include a start location, wherein the start location signifies to a user and/or computing device 120 the initial location of light emitting device 108 prior to emitting light. Template may further receive and/or generate an end location wherein the end location signifies the final location of light emitting device 108. Template may further receive and/or generate a light-emitting path, wherein the light-emitting path is a particular route for light emitting device 108 to follow. In some cases, template may be used to signify to a user and/or a computing device 120 that light-emitting device 108 should start at a particular location on a user's body, follow a predetermined path on the user's body and end in a particular location on the user's body. In some cases, template may receive an area that requires photo modification, wherein template receives and/or generates instructions on how to traverse the particular location that requires photo modification. In some cases, template may receive and/or generate a map signifying to a user and/or a computing device 120 on a particular location and/or set of locations that require photo modification. In some cases, template may receive and/or generate visual data, wherein a user may visually see the projected path for light-emitting device 108. In some cases, data received from template may be in the form of machine-readable data wherein computing device 120 may receive template and make determinations. In some cases, template may generate and/or receive a speed associated with the guidance of light emitting device 108. For example, template may generate a particular speed at which a user and/or computing device 120 is instructed to guide light emitting device over a particular area. In some cases, template may generate and/or receive information received based on a user's movements. For example, a user may draw an intended path wherein computing device may receive the intended path as from template. In some cases, template may receive visual and/or textual data containing instructions on how to guide light emitting device 108 over a particular area. In some cases, a user may interact with an interface as described in this disclosure wherein the user may indicate to computing device 120 a particular path for light emitting device 108.

Still referring to FIG. 1, a "template datum" as used in this disclosure is an element of data of, describing, and/or described by a template. In some cases, template datum 134 may include any elements received and/or generated by template. Template datum 134 may include an area, a border location, border edges, a particular start point, a particular end point, a particular path with an area, a speed along a path, a distance from light emitting device 108 onto the surface that requires photo modification, a time datum, a particular number of repetitions, a pattern and the like, properties of a particular surface that requires photo modification (e.g., skin color, hair color, a body part such as an arm or leg and the like).

Still referring to FIG. 1, template datum may include elements relating to energy densities, energy delivered per second, energy delivered per pulse or emission of light (sometimes known as "shots") and total energy delivered over a particular unit of time. For example, a first template datum may include information indicating that light-emitting device 108 requires 32,500 joules over an area of 325 square centimeters wherein 10 joules may be delivered through each shot over the course of 4 minutes through 2300 shots. In some cases, template may be configured to receive predetermined sets of template datum, wherein each set of template datum may include information relating to the energy densities, energy delivered per second, energy delivered per shot and total energy delivered over a particular unit of time. In some cases, template may receive each set of template datum from a database as described in this disclosure. In some cases, a first set of template datum may include information indicating that a light-emitting device 108 requires 32,500 joules over an area of 325 square centimeters wherein 10 joules may be delivered through each shot or pulse over the course of 4 minutes through 2300 shots, 7 joules, may be delivered through each shot over the course of 5.5 minutes over 3300 shots and/or 5 joules may be delivered through each shot over the course of 8 minutes through 4650 shots. In some cases, a second set of template datum 134 may include information that light emitting device requires 24,000 Joules over an area of 245 square centimeters wherein 10 joules may be delivered over a particular area over the course of 3 minutes the admission of 1750 shots, 7 joules may be delivered over the course of 4 minutes through the admission of 2500 shots and/or 5 joules may be delivered over the course of 6 minutes through the admission of 3500 shots. In some cases, a third set of template datum may include information indicating that light emitting device requires 12,500 joules over an area of 125 square centimeters, wherein 10 joules may be delivered through each shot over the course of 1.5 minutes through the admission of 886 shots, 7 joules through each shot over the course of two minutes through the admission of 1266 shots and/or 5 joules through each shot over the course of 3 minutes through the admission of 1770 shots. In some cases, template datum may include a plurality of predetermined sets of template datum wherein each set may include varying energy densities, varying energy delivered per unit area and the like. In some cases, each set may include a predetermined boundary wherein the predetermined boundary may indicate wherein light emitting device 108 may be guided within.

With continued reference to FIG. 1, as used in this disclosure, "receive" means to accept, collect, or otherwise gather information from the patient, using and/or by a device such as a smartphone, a laptop, a desktop, a tablet, and the like, and/or a that stores such information. In some cases, plurality of user data 132 may be received through an input device and/or a remote device as described in this disclosure. In some cases, input device and/or remote device may be configured to receive data from template and/or template datum 134. In some cases, plurality of user data 132 may be a string containing a plurality of words. In some cases, plurality of user data 132 may be in various format such as, without limitation, txt file, JSON file, word document, pdf file, excel sheet, image, video, audio, and the like thereof. Plurality of user data 132 may include data such as a skin color, a hair color, or an ink color present on the skin of a patient. Skin color may be recorded from the plurality of user data 132 gathered by input device 104 in the form of a skin color datum 136. Skin color datum 136 may be recorded in the form of voltages, wavelengths, still images, moving images or any similar form of data that may be collected from an input device 104. Similarly, the hair color of a user may be recorded from input device 104 as a hair color datum and the ink color on the skin of a user may be recorded as an ink color datum. Further, input device 104 may be used to gather data on the size or boundaries of the user's skin. For example, input device 104 may gather information relating to the size of a person's part to determine the boundaries which the apparatus 100 may be used. The data relating to size or boundaries of the user's skin may be collected as a boundary datum. The boundary datum may be gathered in the form of voltages, wavelengths, still images, moving images or any other suitable form proper for data gathering. Computing device 120 may also be configured to receive video data from input device and generate the plurality of user data 132 from the video data.

With continued reference to FIG. 1, input device 104 and/or computing device 120 may include a sensor, such as and without limitation, a motion sensor. Sensor may include, without limitation, a microelectromechanical system (MEMS) sensor. Sensor may further include, without limitation, an inertial measurement unit (IMU). Sensor may include one or more accelerometers; one or more accelerometers may include a plurality of accelerometers, such as three or more accelerometers positioned to span three dimensions of possible acceleration, so that any direction and magnitude of acceleration in three dimensions may be detected and measured in three dimensions. Sensor may include one or more gyroscopes; one or more gyroscopes may include a plurality of gyroscopes, such as three or more gyroscopes positioned to span three dimensions of possible acceleration, so that any direction and magnitude of change in angular position in three dimensions may be detected and measured in three dimensions. Sensor may include, without limitation magnetic sensors such as Hall effect sensors, compasses such as solid-state compasses, or the like. Persons skilled in the art, upon reviewing the entirety of this disclosure, will be aware of various components and/or devices that may be used as sensor consistently with this disclosure. In some cases, data gather by sensor may be used as some or all of plurality of user data 132. In some cases, template datum 134 may be received through a sensor, wherein template contains and/or receives movements of sensor. In some cases, sensor may receive data associated with the movements of a user, wherein the movements may indicate a particular path for light emitting device 108. In some cases, sensor may be configured to receive elements within template, such as and without limitations, a start location, an end location, a particular path for the light emitting device to be guided on, a distance from the surface requiring photo modification to the light emitting device, a speed datum indicating the speed at which the guide the light emitting device, a time datum indicating the amount time spent on a particular area, a repetition datum indicating the amount of repetitions and the like.

Continuing to reference FIG. 1, processor 124 may use an image classifier to identify a key image in plurality of user data 132. As used herein, a "key image" is an element of visual data used to identify and/or match elements to each other. An image classifier may be trained with binarized visual data that has already been classified to determine key images in plurality of user data 132. An image classifier may be consistent with any classifier as discussed herein. An image classifier may receive an input of plurality of user data 132 and output a key image of plurality of user data 132. An identified key image may be used to locate a data entry relating to the image data in plurality of user data 132, such as skin color. In an embodiment, image classifier may be used to compare visual data in plurality of user data 132 with visual data in another data set, such as previously inserted user data. In the instance of a video, processor 124 may be used to identify a similarity between videos by comparing them. processor 124 may be configured to identify a series of frames of video. The series of frames may include a group of pictures having some degree of internal similarity, such as a group of pictures having similar color profiles. In some embodiments, comparing series of frames may include video compression by inter-frame coding. The "inter" part of the term refers to the use of inter frame prediction. This kind of prediction tries to take advantage of temporal redundancy between neighboring frames enabling higher compression rates. Video data compression is the process of encoding information using fewer bits than the original representation. Any compression may be either lossy or lossless. Lossless compression reduces bits by identifying and eliminating statistical redundancy. No information is lost in lossless compression. Lossy compression reduces bits by removing unnecessary or less important information. Typically, a device that performs data compression is referred to as an encoder, and one that performs the reversal of the process (decompression) as a decoder. Data compression may be subject to a space-time complexity trade-off. For instance, a compression scheme for video may require expensive hardware for the video to be decompressed fast enough to be viewed as it is being decompressed, and the option to decompress the video in full before watching it may be inconvenient or require additional storage. Video data may be represented as a series of still image frames. Such data usually contains abundant amounts of spatial and temporal redundancy. Video compression algorithms attempt to reduce redundancy and store information more compactly.

Still referring to FIG. 1, inter-frame coding may function by comparing each frame in the video with another frame, which may include a previous frame. Individual frames of a video sequence may be compared between frames, and a video compression codec may send only the differences from a reference frame for frames other than the reference frame. If a frame contains areas where nothing has moved, a system may issue a short command that copies that part of a reference frame into the instant frame. If sections of a frame move in manner describable through vector mathematics and/or affine transformations, or differences in color, brightness, tone, or the like, an encoder may emit a command that directs a decoder to shift, rotate, lighten, or darken a relevant portion. An encoder may also transmit a residual signal which describes remaining more subtle differences from reference frame, for instance by subtracting a predicted frame generated through vector motion commands from the reference frame pixel by pixel. Using entropy coding, these residual signals may have a more compact representation than a full signal. In areas of video with more motion, compression may encode more data to keep up with a larger number of pixels that are changing. As used in this disclosure, reference frames are frames of a compressed video (a complete picture) that are used to define future frames. As such, they are only used in inter-frame compression techniques. Some modern video encoding standards, such as H.264/AVC, allow the use of multiple reference frames. This may allow a video encoder to choose from more than one previously decoded frame on which to base each macroblock in another frame.

Further referring to FIG. 1, receiving plurality of user data 132 may include detecting a shape using an image recognition algorithm identifying the detected shape as the particular area that requires photo modification, such as an arm. Image recognition algorithm may include an edge-detection algorithm, which may detect one or more shapes defined by edges. An "edge detection algorithm," as used in this disclosure, includes a mathematical method that identifies points in a digital image at which the image brightness changes sharply and/or has discontinuities. In an embodiment, such points may be organized into straight and/or curved line segments, which may be referred to as "edges." Edge detection may be performed using any suitable edge detection algorithm, including without limitation Canny edge detection, Sobel operator edge detection, Prewitt operator edge detection, Laplacian operator edge detection, and/or Differential edge detection. Edge detection may include phase congruency-based edge detection, which finds all locations of an image where all sinusoids in the frequency domain, for instance as generated using a Fourier decomposition, may have matching phases which may indicate a location of an edge. Edge detection may be used to detect body parts and/or surfaces that require photo modification. Edge detection may further be used to determine the boundaries of the surfaces requiring phot modification as indicated in boundary datum. In some cases, computing device may determine boundary datum using edge detection.

With continued reference to FIG. 1, computing device 120 is configured to generate a plurality of light emission parameters 140 from the one or more light settings 112 as a function of the plurality of user data 132. "Plurality of light emission parameters" as described in this disclosure is the data corresponding to the one or more settings 112 on the light-emitting device 108. For example, Plurality of light emission parameters 140 may contain a power density datum corresponding to the power density setting 116 on light-emitting device 108. In some embodiments plurality of light emission parameters 140 may include the power density datum, the wavelength datum, the pulse width datum, the cooling datum and the repetition datum. "Repetition datum" as defined in this disclosure is data referring to required repetitions for proper tissue photo modification by light-emitting device 108. For example, a user may need to guide light-emitting device 108 over a specified area several times before the chromophores are properly destroyed. Repetition datum may change depending on the body part. For example, repetition datum may require different repetition for photo modification on a user's arm as compared to the patient's back. Repetition may contain numeric digits correlating to the number of repetitions required. Repetition datum may also contain instructions on how to guide light-emitting device over a patient's skin.

Continuing to reference FIG. 1, computing device 120 may use a machine learning module, to implement one or more algorithms or generate one or more machine-learning models, such as light emission learning model, to calculate at least one plurality of light emission parameters. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from a database, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. A light emission module may be used to generate light emission machine learning model 144 and/or any other machine learning model using training data. Light emission machine learning model 144 may be trained by correlated inputs and outputs of training data. Training data may be data sets that have already been converted from raw data whether manually, by machine, or any other method. Training data May include previous outputs such that light emission machine learning model 144 iteratively produces outputs. Light emission machine learning model 144 using a machine-learning process may output converted data based on input of training data. In an embodiment, analyzing the user profile comprising the plurality of user related data may include determining the plurality of light emission parameters using a machine learning model, such as light emission machine learning model 144 generated by light emission module. Light emission machine learning model 144 may be trained by training data, discussed in further detail below, such as light emission training data 148. Light emission training data 148 may be stored in database 152.

Still referring to FIG. 1, database 152 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database 152 may include a plurality of data entries and/or records as described above. Data entries in a database 152 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, determining the plurality of light emission parameters 140 based on the plurality of user data 132 using a light emission machine learning model 144 may include receiving light emission machine learning model 144. In an embodiment, light emission machine learning model 144 may include multiple data sets of plurality of user data 132 that are each correlated to one of multiple data sets of plurality of light emission parameters 140. For example, light emission machine learning model 144 may provide a specific power based on the skin color datum 136 present in plurality of user data 132. In an exemplary embodiment, plurality of light emission parameters 140 may aid in the process of determining the one or more settings on light-emitting device 108. Light emission machine learning model 144 may be stored or retrieved from a database as described above. Light emission training data 148 may be generated using previous inputs and outputs as described above. Determining the plurality of light emission parameters 140 using a machine learning model may further include training a light emission machine learning model 144 as a function of light emission machine learning model 144. Further, determining plurality of light emission parameters 140 using a machine learning model may also include determining at least one plurality of light emission parameters using trained light emission machine learning model 144.

Still referring to FIG. 1, computing device 120 may be configured to generate a light emission optimization model 156. In one embodiment, light emission optimization model 156, may include at least an optimization criterion 160. An "optimization criterion" as used in this disclosure, is a value that is sought to be maximized or minimized in a process. For instance, in a non-limiting example, optimization criterion 160 may include any description of a desired value or range of values for one or more attributes of an optimized plurality of light emission parameters; desired value or range of values may include a maximal or minimal value, a range between maximal or minimal values, or an instruction to maximize or minimize an attribute. Optimization criterion 160 may include a ranked list of the at least one plurality of light emission parameters 140 with adherence to the plurality of user data 132. For example, computing device 120 may generate an ordered list ranking each of the at least one plurality of user data 132 in order of efficacy or safety. Such a list may indicate a first plurality of light emission parameters with the greatest probability of hair removal and the smallest probability of discomfort. Such a list may further indicate a second or third plurality of light emission parameters with smaller efficacy results or a larger probability of discomfort. Optimization criterion 160 may further specify a range of suitable power density setting 116. In a non-limiting example, optimization criterion 160 may specify a range of wavelength settings dependent on the patient's skin color needed to prevent skin damage while still targeting specific chromophores on the patient's skin. In another non-limiting example, optimization criterion 160 may specify one or more tolerances for each range. In yet another non-limiting example, optimization criterion 160 may assign weights to different settings such as the power density setting 116, the wavelength setting, and the pulse width setting. In an embodiment, computing device 120 may be configured to generate an adherence score for the at least one plurality of light emission parameters. Optimization may include optimizing a plurality of optimization criteria and/or a function and/or combination of optimization criteria.

With continued reference to FIG. 1, in some embodiments, processor 124 may be configured to compare any data, and/or optimize any factor and/or parameter, such as the plurality of light emission parameters 108, as described throughout this disclosure using an objective function. For instance, computing device 120 may generate an objective function and an adherence score using the objective function. An "objective function" as used in this disclosure is a process of minimizing or maximizing one or more values based on a set of constraints. In some embodiments, an objective function of computing device 120 may include the optimization criterion described above. As a non-limiting example, an optimization criterion may specify that an impact factor should be within a 1% difference of optimization criterion. An optimization criterion may alternatively request that an impact factor be greater than a certain value. An optimization criterion may specify one or more tolerances for deviation from the datum within the plurality of light emission parameters 140. In some embodiments, light emission optimization model 156 may be formulated as a linear objective function. Light emission optimization model 156 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all user data r, S is a set of all light emission parameters S, $c_{rs}$ is a score of a pairing of a given user data with a given light emission parameter, and $x_{rs}$ is 1 if a user data r is paired with a light emission parameter s, and 0 otherwise. The coefficients or biases may further be tuned using a machine learning model as described in this disclosure. Continuing the example, constraints may specify that each plurality of light emission parameters 140 is assigned to only one skin type, and each skin type is assigned only one plurality of light emission parameters 140. Plurality of light emission parameters 140 may include any parameters as described above. Plurality of light emission parameters 140 may be optimized for a maximum score combination of all generated skin selections. In various embodiments, a light emission optimization model 156 may determine a combination of different settings for the light-emitting device 108 that maximizes a total score subject to a constraint that each plurality of light emission parameters 140 is paired to exactly one skin type. In some embodiments, Light emission optimization model 156 may determine a combination of different settings for light-emitting device 108 that maximizes a total score subject to constraints for each specific skin type such as a maximum total energy delivered per square unit area, minimum energy delivery values, minimum energy values for each specific follicle, minimum wavelength requirements, minimum or maximum spot size requirements and the like. An optimal parameter set within the bounds of the constraints may be found using an objective function or a loss function as described in this disclosure. Not all skin types may receive a plurality of light emission parameters 140 pairing since each user may only receive one plurality of light emission parameters 140. A mathematical solver may be implemented to solve for the set of feasible pairings that maximizes the sum of scores across all pairings; mathematical solver may be implemented on computing device 120 and/or another device in apparatus 100, and/or may be implemented on third-party solver.

With continued reference to FIG. 1, computing device 120 may be configured to minimize a loss function, where a "loss function" is an expression an output of which an optimization model minimizes to generate an optimal result. As a non-limiting example, processor 124 may assign variables relating to a set of parameters, which may correspond to score plurality of light emission parameters 140 as described above, calculate an output of mathematical expression using the variables, and select a pairing that produces an output having the lowest size, according to a given definition of "size," of the set of outputs representing each of plurality of candidate setting combinations; power density may, for instance, include absolute value, numerical size, or the like. Selection of different loss functions may result in identification of different potential pairings as generating minimal outputs. Objectives represented in an objective function and/or loss function may include minimization of discomfort. Objectives may include prolonged efficacy of using high intensity lights or lasers. Objectives may also include minimization of potential burns using a specific power density or wavelength. Computing device 120 may use a machine-learning model as described in this disclosure to generate optimization criteria and/or objective functions.

Continuing to reference FIG. 1, computing device 120 may be configured to determine a range of parameters based on the plurality of user data 132. In an embodiment, plurality of light emission parameters 140 may include a plurality of different types of data that may be matched to the same type of data in plurality of user data 132. An aggregate plurality of light emission parameters 140 may be created using a fuzzy inference system, where the degrees of match are represented by fuzzy sets, and inferencing rules propagate degrees of match to output fuzzy sets and/or scores. Fuzzy sets may be fine-tuned using any machine-learning model as discussed herein. Fuzzy sets are discussed in detail in FIG. 3.

Still referring to FIG. 1, computing device 120 may be configured to provide a recommendation of plurality of light emission parameters 140 to a patient. In some embodiments, computing device 120 may receive user feedback about regarding the recommendation of plurality of light emission parameters 140 such as prior user experience including burns, side effects, and the like, and actual outcomes hair removal. Computing device 120 may update a recommendation of the plurality of light emission parameters 140 as a function of user feedback. Computing device 120 may further be configured to turn the feedback into training data, for instance and without limitation by correlating user inputs, parameters, outcome data as entered by users and/or automatically recorded, or the like, with any other such values; training data may include without limitation any training data disclosed in this disclosure. The training data may then be used to update or retrain the machine-learning model. In some embodiments, computing device 120 may be configured to allow adjustments of percentage of each setting as a function of user feedback, such as a range of power density setting 116s, wavelength settings, and pulse width settings.

Still referring to FIG. 1, processor 124 may be configured to compare the plurality of light emission parameters 140 to a safety threshold. A "safety threshold," as described herein, is a quantitative datum or collection of data representing a maximal or minimal value consistent with safe operation of an apparatus 100 and the plurality of light emission parameters 140 input into an apparatus 100, for one or more parameters. Safety threshold may include a single numerical value, a vector or n-tuple of numerical values, and/or any other suitable representation. For example, A safety threshold may include a maximum power density setting 116 or a minimum wavelength that may not be exceed.

Still referring to FIG. 1, computing device 120 is configured to modify a user interface 164 as a function of the plurality of light emission parameters 140. As used in this disclosure, a "user interface" is a form of interface that is visible to the user and allows users to interact with apparatus 100 through one or more interaction components. In a non-limiting example, user interface 164 may be a graphical user interface (GUI). In some cases, user interface may contain an interaction component such as, without limitation, button, link, image, video, audio, and the like thereof. In some embodiments, interaction component may include one or more menus and/or panels permitting selection of data to be displayed and/or used, elements of data, functions, or other aspects of data to be edited, added, and/or manipulated, or the like. Persons skilled in the art, upon reviewing the entirety of this disclosure, will be aware of various ways in which a user interface 164 and/or interaction component thereof may be implemented and/or used as described in this disclosure. In some embodiments, without limitation, user interface 164 may be configured to present any data/information described in this disclosure such as, without limitation, plurality of user data 132, skin color datum 136, plurality of light emission parameters 140, and the like thereof. In a non-limiting example, a user interface 164 may be a web page displaying plurality of light emission parameters 140.

With continued reference to FIG. 1, processor 124 and/or computing device 120 is configured to transmit a light command as a function of user input with user interface 164. "Command" for the purposes of this disclosure is an instruction or set of instructions given to a computing device to perform a function. "Light command" for the purposes of this disclosure is an instruction used to operate light emitting device 108. Light command may include a command to emit a light from light emitting device 108. In some cases, light command may include a command to instruct an automated arm and/or light emitting device 108 to guide the automated arm over a particular area wherein light emitting device 108 may perform photo modification. In some cases, light command contains instructions to emit a light from light emitting device 108. In some cases, light command contains instructions to stop emitting light from light emitting device. In some cases, light command may include instructions to begin a photo modification process, such as the operation of an automated arm and the like. A user may interact with user interface 164 wherein a light command may be sent from computing device 120 as a function of user input. In some cases, a user may select a button wherein selection of the button instructs computing device 120 to send a light command and begin a photo modification process. In some cases, light command may be viewed as a button on a use interface, wherein selection of the button instructs computing device 120 to output a light command. In some cases, light command may include instructions to operate light emitting device 108 based on the plurality of light emission parameters. For example, light command may include instructions configuring light emitting device 108 to operate on a particular power setting, wavelength, and the like. In some cases, computing device 120 and/or user interface 164 is configured to transmit light command to light emitting device 108.

With continued reference to FIG. 1, in some embodiments, user interface 164 may allow user to provide data submission through one or more interaction components. As used in this disclosure, a "data submission" is an assemblage of data provided by the user as an input source. In a non-limiting example, data submission may include user uploading one or more documentations to processor 124. As used in this disclosure, a "documentation" is a source of information. In some cases, documentation may include electronic document, such as, without limitation, txt file, JSON file, word document, pdf file, excel sheet, image, video, audio, and the like thereof. In other cases, documentation may include a simple data structure, such as without limitation, integer, string, Boolean, any data structure described in this disclosure, and the like thereof. In a non-limiting example, documentation may include a user's identification document such as, without limitation, driver license number, picture of user's passport, and the like thereof.

With continued reference to FIG. 1, in some embodiments, interaction component may include an event handler configured to receive at least an event. As used in this disclosure, an "event handler" is an element that operates asynchronously once an event take place. In some cases, event handler may include routine, wherein the routine is a sequence of code that is intended to be called and executed repeatedly when apparatus 100 is running. In a non-limiting example, event handler may include a callback routine, wherein the callback routine may dictate one or more action that follows event. As used in this disclosure, an "event" is an action that take place when the user interacts with apparatus 100, interface, user interface 164, interaction component, and/or any other components/devices that user may interact with. In a non-limiting example, event may include, without limitation, clicking, holding, pressing, tapping, swiping and the like thereof. In some embodiments, an event may change a state of interaction component. In a non-limiting example, event may change the state of an interaction component from "inactive" (i.e., unchecked) to "active" (i.e., checked), wherein the interaction component may include a checkbox. In some cases, an event may include a plurality of actions. In other cases, an event may involve other interactive devices such as, without limitation, mouse, keyboard, interface, headphone, any other interactive device that either electrically and/or communicatively connected to apparatus 100, and the like thereof. In a non-limiting example, user may interact with interaction component through performing an event on a user interface 164, wherein the event may include user clicking a checkbox present on the user interface 164. In some embodiments, event handler may utilize one or more application program interface such as, without limitation, web events and the like thereof. Additionally, or alternatively, event handler may operate any processing step described in this disclosure. In a non-limiting example, plurality of light emission parameters 140 may include an event handler, wherein the event handler may initialize a data structure such as, without a limitation, a dictionary and/or store selected plurality of light emission parameters 140 in the dictionary once a click action is performed on an interaction component such as, without limitation, a checkbox.

Still referring to FIG. 1, apparatus 100 may include an augmented reality device. An "augmented reality" device, as used in this disclosure, is a device that permits a user to view a typical field of vision of the user and superimposes virtual images on the field of vision. Augmented reality device may be used for training sessions or for virtual tissue photo modifications. Augmented reality device may be configured to capture a field of vision of the user and display an augmented visual field to the user. Augmented reality device may capture at least image of a field of vision of a user. Augmented visual field then may then display a visual guide datum to the user such that the user may follow the visual guide when guiding the light-emitting device 108. "Visual guide datum" as described in the disclosure is a computer-generated visual guide that directs the user as to how to perform various functions. For example, visual guide datum may contain a digital arrow on the augmented visual field directing the user to guide the light-emitting device 108 along a predetermined path. Visual guide datum may also contain a series of alpha-numeric instructions displayed on the augmented visual field, educating the user on how to guide the light-emitting device 108 along the predetermined area. Visual guide datum may be calculated as a function of the plurality of user data 132 from input device 104 such as the skin color datum 136 and the hair color datum. Visual guide datum may also be calculated as a function of the at least an image of the field of view of the user and the skin color datum 136. Apparatus may incorporate augmented reality device described below.

Still referring to FIG. 1, computing device 120 may also be configured to output a plurality of body parameters based on the boundary datum. "Plurality of body parameters" refer to the boundaries of a patient's body or the boundaries as to which the light should be emitted onto the body. For example, the plurality of body parameters may include data relating to the boundaries of a patient's arm or leg, or the boundaries of a tattoo on a patient's skin. Plurality of body parameters aid the user in determining which skin tissue requires light and which do not. Plurality of boundary parameters may also be employed to provide an optimal route for the tissue photo modification on a patient's skin. For example, computing device 120 may generate an optimal route for the user to guide the light-emitting device 108 such that the skin removal or the tattoo removal is more efficient. Determining the plurality of body parameters based on the boundary datum using a boundary machine learning model may include receiving boundary training data. In an embodiment, boundary training data may include a plurality of boundary datum that are each correlated to multiple data sets of plurality of body parameters. For example, boundary training data may provide a specific boundary detailing a user's arm or detailing a specific area that needs tissue photo modification based on the boundary datum received. Boundary training data may be generated using previous inputs and outputs as described above. Determining the plurality of body parameters using a machine learning model may further include training a boundary machine learning model as a function of boundary training data. Further, determining plurality of body parameters using a machine learning model may also include determining at least one plurality of body parameters using trained body machine learning model.

Still referring to FIG. 1, apparatus 100 may include a notification system. "Notification system" as used in the disclosure refers to the notification of the user of the apparatus 100 that an event has occurred. For example, the user may be notified when the light-emitting device 108 focuses on an area for too long. The user may also be notified if the light-emitting device 108 has been guided beyond a predetermined area calculated by the plurality of body parameters. "Predetermined area" as used in the disclosure refers to the area the light-emitting device 108 will be guided over. For example, the user may wish to provide light on only one area of a patient's arm and not another. The predetermined area may be calculated by the plurality of plurality of boundary parameters. Notification system may be a pop-up screen on a user display, a flashing light on the light-emitting device 108, or even a sound from a speaker connected to the computing device 120. Notification system may also be used to notify a user when user has exceeded a repetition threshold. "Repetition threshold" as described in this disclosure is the maximum number of repetitions of lighting emitting device on a user that may be suggested or allowed for a particular user. For example, a repetition threshold may indicate that a maximum of three repetitions are suggested or allowed for a particular user. Any further increase in repetitions may cause harm to the user or may result in improper tissue photo modification. In some cases, notification system may be configured to notify a user when a threshold has been exceeded. The threshold may be associated with any data as described in this disclosure. for example, notification system may notify a user if a power setting is higher than the power setting as indicated in plurality of light parameters. In some cases, the threshold may include datum described within this disclosure wherein notification system may notify a user when one or more datum within plurality of light emission parameters 140 has been exceed. In some embodiments, threshold may depend on template datum 134. In some cases, notification system may notify a user when a light emitting device 108 is being guided too quickly in comparison to the speed received by template or as indicated by template datum 134. Additionally or alternatively notification system may notify a user when a template datum 134 received by template has been exceeded, such as a user exceeding the bounds provided within template datum 134 and the like. In some cases, notification system may be dependent on template datum 134 wherein notification system may notify a user when a user has exceeded a particular number or parameter within template datum 134. For example, a notification system may notify a user when a boundary indicated within template datum 134 has been exceeded. In another non-limiting example, if template defines and/or generates a smaller surface area, a particular energy threshold may be lower, as a result, a user may be notified when a particular energy threshold has been exceeded. In yet another non-limiting example, a particular template datum 134 received and/or generated by template may indicate a particular speed, start location, stop location and the like, wherein notification system may notify a user when light emitting device 108 begins and/or ends at a location different from that described within template datum 134. In yet another non-limiting example, a particular template datum 134 may describe boundaries and/or edges, wherein notification system may notify a user when light emitting device has been guided beyond a particular edge and/or boundary described within template datum 134. In some cases, notification system may further notify a user, when light emitting device 108 is guided at a speed different from that described within template datum 134. In some cases, notification system may depend on template and/or template datum 134 such that a user may be notified when light emitting device is guided over a differing path than the one described by template and/or template datum 134. In some cases, plurality of light emission parameters 140 may be generated as function of template and/or template datum 134 wherein notification system may depend on one or more elements within plurality of light emission parameters 140. For example, a user may exceed a particular light emission parameter wherein notification system may notify a user. In some cases, notification may include textual and/or visual data displayed to a user, wherein the user may be aware of the particular scope or bound exceeded. In some cases notification system may include audio wherein a user may be notified by a sound when a particular scope and/or bound has been exceeded. In some cases, notification system may notify a user when a particular boundary, edge location and the like has not been satisfied as generated and/or received by template. For example, a notification system may notify a user when a particular area has not been properly photo modified by light emitting device 108.

Continuing to refer to FIG. 1, apparatus 100 may include a shutoff switch. A shutoff switch as defined in the disclosure is any switch, push button or similar mechanism that can deactivate the light-emitting device 108. The shutoff switch may also be automatic such that the computing device 120 activates the shutoff switch when an event occurs. For example, shutoff switch may be activated when the repetition threshold has been exceeded by a predetermined amount. An automatic shutoff switch aids in the prevention of burns or unwanted light therapy by the user onto a patient.

Continuing to refer to FIG. 1, Apparatus 100 may include an automated arm. "Automated arm" as described in the disclosure refers to a mechanical arm capable of movement along a predetermined area. Automated arm may be attached to the laser-emitting device and used to guide the laser emitting device along a predetermined area. Automated arm removes the need for a user to manually control the light-emitting device 108. Instead, automated arm may be controlled using the computing device 120. As described above, computing device 120 may utilize machine learning to guide the automated arm along a predetermined area. The boundary datum may be used to guide the arm within a designated area. Automated arm may be utilized in a similar fashion to a computer controlled cutting tool. Automated arm may utilize computing device 120 to generate a light path such that automated arm moves along a predetermined route.

With continued reference to FIG. 1, light emitting device 108 may be guided over a particular area using mirror scanning. "Mirror scanning" for the purposes of this disclosure is a process in which emitted light may be guided using a mirror. For example, a light from light emitting device 108 may be pointed at a mirror wherein movement of the mirror may guide the light reflected off of the mirror. The mirror being used is referred to as a scanning mirror. The scanning mirror is configured to receive a light beam and redirect the light beam to a particular area. In some cases, the scanning mirror may be used to guide a light beam from light emitting device 108 over a particular surface area for photo modification. In some cases, scanning mirror may include motorized controls wherein scanning mirror can be adjusted through a series of commands. Scanning mirror may include a motor, wherein the motor is configured to linearly and/or angularly rotate scanning mirror in order to guide a light from light emitting device. In some cases, scanning mirror may be consistent with automated arm. In some cases automated arm includes scanning mirror wherein automated arm is configured to rotate scanning mirror for use in photo modification.

With continued reference to FIG. 1, apparatus may include micro-electro-mechanical systems (MEMS) and/or MEM technology. MEMS may allow miniaturized mechanical, electro-mechanical, and optical comments on a microscale. Apparatus 100 may include MEMS devices such as sensors, pressure sensors, temperature sensors, accelerometers, gyroscopes, microphones, and the like in order to perform any necessary determinations as discussed above. In some cases, apparatus 100 may include MEMS devices such as mirrors, lenses, and the like. In some cases, MEMS devices may be used to receive plurality of user data as described above. In some cases, MEMS mirrors may be used to perform a sweep of a particular area and guide light emitting device. In some cases, apparatus may include a first mirror to guide light emitting device 108 in a horizontal direction, and a second mirror to guide light emitting device 108 in a vertical direction. In some cases, mirrors may be used in concert to guide light emitting device 108. In some cases, the mirrors may be connected to moveable arms wherein the moveable arms may be used to rotate and/or move the mirrors to guide light emitting device 108. In some cases, the moveable arms may be configured to move in response to a command and/or signal. In some cases, computing device may transmit a command wherein the movable arms may move based on the command. In some cases, moveable arms may be used to increase the precision of a light reflected on a surface by light emitting device. In some cases, the movable arms may be used to increase the precision of the photo modification.

Figure 2:
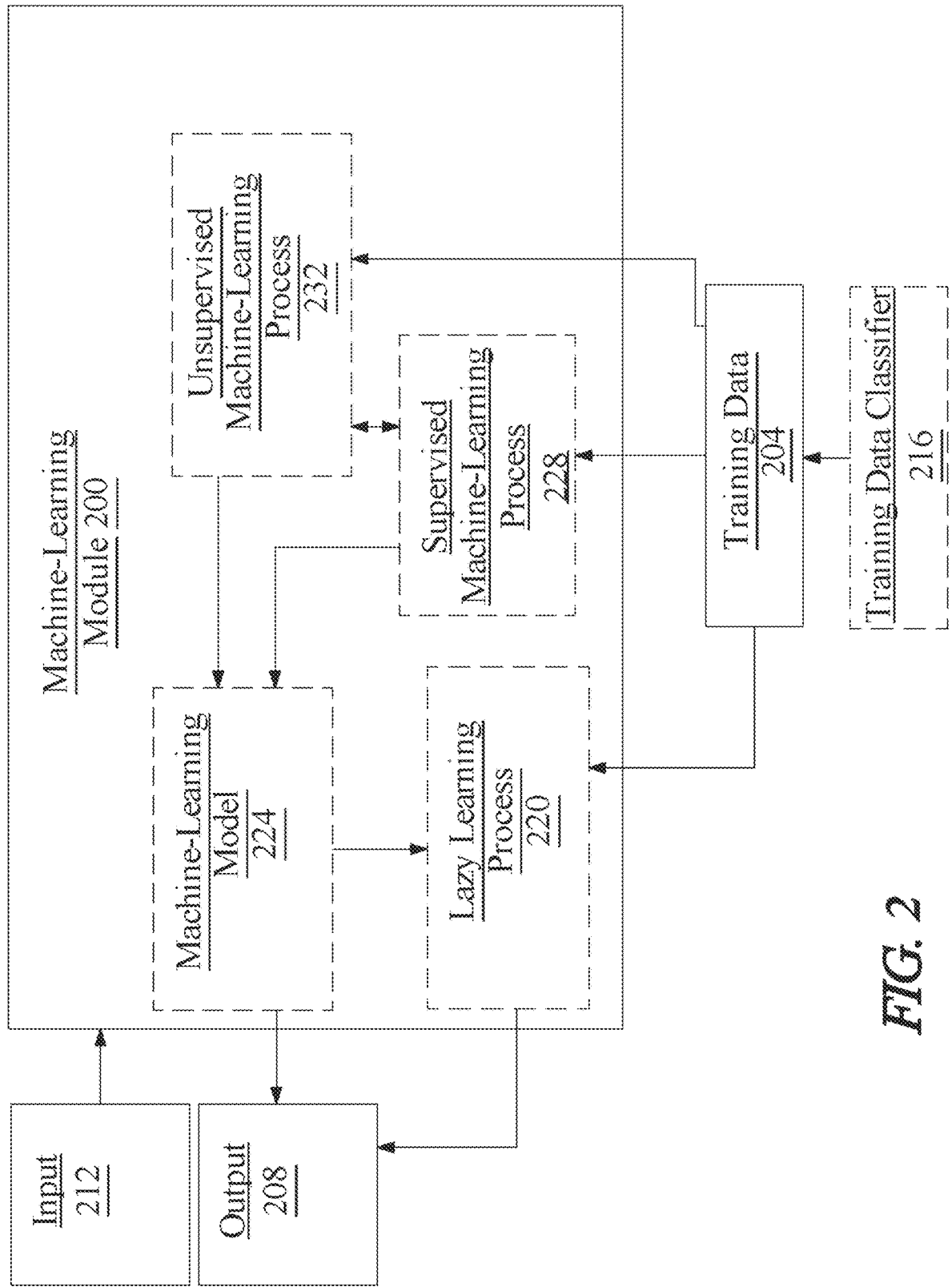
FIG. 2 is a block diagram of an exemplary embodiment of a machine learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, and outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 3:
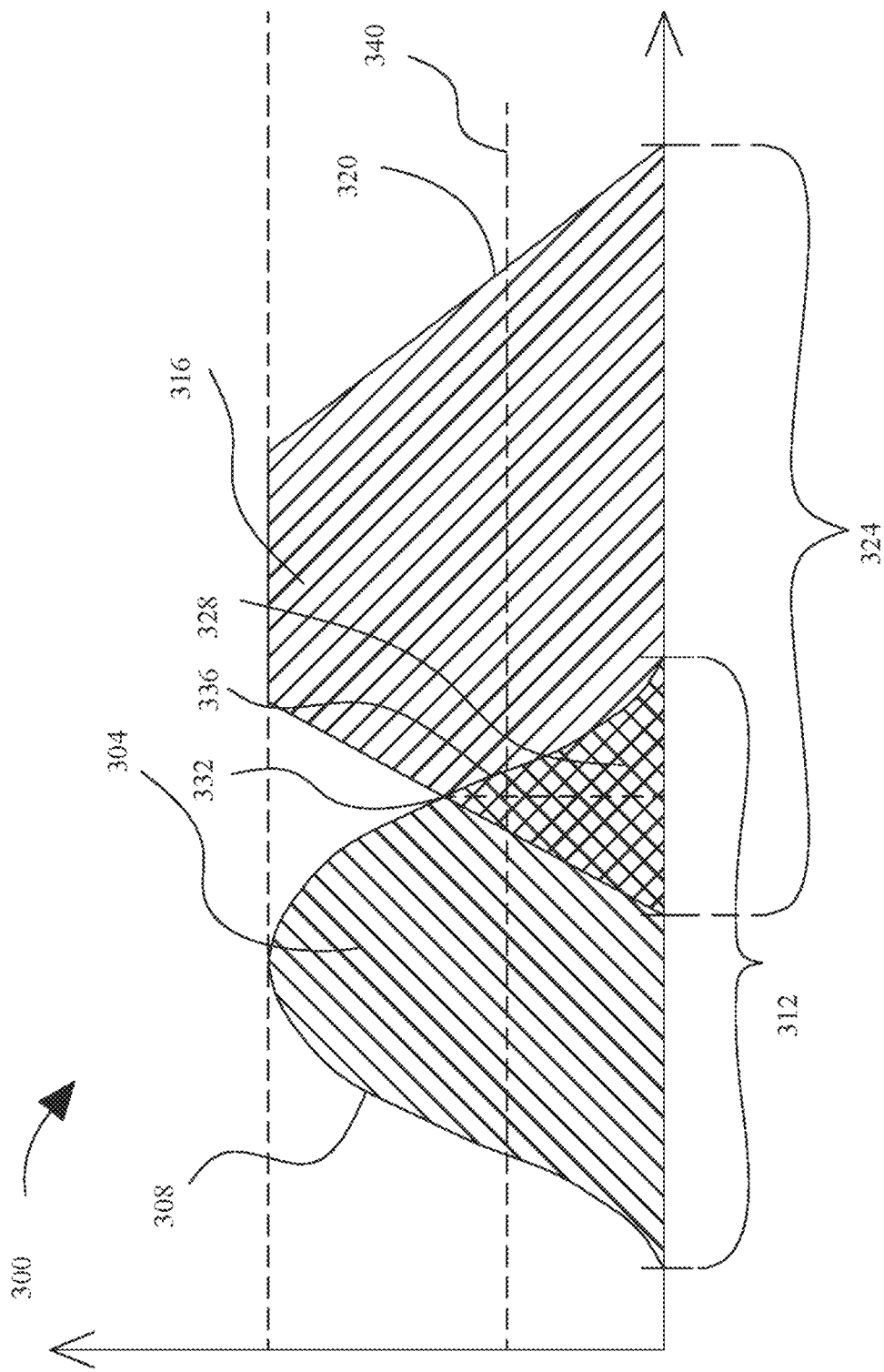
FIG. 3 is a diagram of an exemplary embodiment of a fuzzy set inference system.

Referring to FIG. 3, an exemplary embodiment of fuzzy set comparison 300 is illustrated. A first fuzzy set 304 may be represented, without limitation, according to a first membership function 308 representing a probability that an input falling on a first range of values 312 is a member of the first fuzzy set 304, where the first membership function 308 has values on a range of probabilities such as without limitation the interval [0, 1], and an area beneath the first membership function 308 may represent a set of values within first fuzzy set 304. Although first range of values 312 is illustrated for clarity in this exemplary depiction as a range on a single number line or axis, first range of values 312 may be defined on two or more dimensions, representing, for instance, a Cartesian product between a plurality of ranges, curves, axes, spaces, dimensions, or the like. First membership function 308 may include any suitable function mapping first range 312 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 3, first fuzzy set 304 may represent any value or combination of values as described above, including output from one or more machine-learning models and the plurality of light emission parameters. A second fuzzy set 316, which may represent any value which may be represented by first fuzzy set 304, may be defined by a second membership function 320 on a second range 324; second range 324 may be identical and/or overlap with first range 312 and/or may be combined with first range via Cartesian product or the like to generate a mapping permitting evaluation overlap of first fuzzy set 304 and second fuzzy set 316. Where first fuzzy set 304 and second fuzzy set 316 have a region 328 that overlaps, first membership function 308 and second membership function 320 may intersect at a point 332 representing a probability, as defined on probability interval, of a match between first fuzzy set 304 and second fuzzy set 316. Alternatively or additionally, a single value of first and/or second fuzzy set may be located at a locus 336 on first range 312 and/or second range 324, where a probability of membership may be taken by evaluation of first membership function 308 and/or second membership function 320 at that range point. A probability at 328 and/or 332 may be compared to a threshold 340 to determine whether a positive match is indicated. Threshold 340 may, in a non-limiting example, represent a degree of match between first fuzzy set 304 and second fuzzy set 316, and/or single values therein with each other or with either set, which is sufficient for purposes of the matching process; for instance, threshold may indicate a sufficient degree of overlap between an output from one or more machine-learning models and/or plurality of light emission parameters and a predetermined class, such as without limitation a light emission categorization, for combination to occur as described above. Alternatively or additionally, each threshold may be tuned by a machine-learning and/or statistical process, for instance and without limitation as described in further detail below.

Further referring to FIG. 3, in an embodiment, a degree of match between fuzzy sets may be used to classify a plurality of user data with plurality of light emission parameters. For instance, if a plurality of light emission parameters has a fuzzy set matching plurality of user data fuzzy set by having a degree of overlap exceeding a threshold, computing device 120 may classify the plurality of user data as belonging to the plurality of light emission parameters categorization. Where multiple fuzzy matches are performed, degrees of match for each respective fuzzy set may be computed and aggregated through, for instance, addition, averaging, or the like, to determine an overall degree of match.

Still referring to FIG. 3, in an embodiment, a plurality of user data may be compared to multiple plurality of light emission parameters categorization fuzzy sets. For instance, plurality of user data may be represented by a fuzzy set that is compared to each of the multiple plurality of light emission parameters categorization fuzzy sets; and a degree of overlap exceeding a threshold between the plurality of user data fuzzy set and any of the multiple plurality of light emission parameters categorization fuzzy sets may cause computing device 120 to classify the plurality of user data as belonging to plurality of light emission parameters categorization. For instance, in one embodiment there may be two plurality of light emission parameters categorization fuzzy sets, representing respectively plurality of light emission parameters categorization and a plurality of light emission parameters categorization. First plurality of light emission parameters categorization may have a first fuzzy set; Second plurality of light emission parameters categorization may have a second fuzzy set; and plurality of user data may have a plurality of user data fuzzy set. computing device 120, for example, may compare a plurality of user data fuzzy set with each of plurality of light emission parameters categorization fuzzy set and in plurality of light emission parameters categorization fuzzy set, as described above, and classify a plurality of user data to either, both, or neither of plurality of light emission parameters categorization nor in the plurality of light emission parameters categorization. Machine-learning methods as described throughout may, in a non-limiting example, generate coefficients used in fuzzy set equations as described above, such as without limitation x, c, and σ of a Gaussian set as described above, as outputs of machine-learning methods.

Still referring to FIG. 3, a computing device may use a logic comparison program, such as, but not limited to, a fuzzy logic model to determine a plurality of light emission parameters response. An plurality of light emission parameters response may include, but is not limited to, similar, not similar and the like; each such plurality of light emission parameters response may be represented as a value for a linguistic variable representing plurality of light emission parameters response or in other words a fuzzy set as described above that corresponds to a degree of as calculated using any statistical, machine-learning, or other method that may occur to a person skilled in the art upon reviewing the entirety of this disclosure. In other words, a given element of plurality of user data may have a first non-zero value for membership in a first linguistic variable and a second non-zero value for membership in a second linguistic variable value. In some embodiments, determining a plurality of light emission parameters categorization may include using a linear regression model. A linear regression model may include a machine learning model. A linear regression model may be configured to map data of plurality of user data, such as degree of compatibility to one or more plurality of light emission parameters considerations. A linear regression model may be trained using a machine learning process. A linear regression model may map statistics such as, but not limited to, quality of plurality of user data compatibility. In some embodiments, determining plurality of light emission parameters of plurality of user data may include using a plurality of light emission parameters classification model. A plurality of light emission parameters classification model may be configured to input collected data and cluster data to a centroid based on, but not limited to, frequency of appearance, linguistic indicators of quality, and the like. Centroids may include scores assigned to them such that quality of compatibility of plurality of user data may each be assigned a score. In some embodiments plurality of light emission parameters classification model may include a K-means clustering model. In some embodiments, plurality of light emission parameters classification model may include a particle swarm optimization model. In some embodiments, determining the plurality of light emission parameters of a plurality of user data may include using a fuzzy inference engine. A fuzzy inference engine may be configured to map one or more plurality of user data record elements using fuzzy logic. In some embodiments, plurality of user data may be arranged by a logic comparison program into plurality of light emission parameters arrangement. An "plurality of light emission parameters arrangement" as used in this disclosure is any grouping of objects and/or data based on skill level and/or output score. This step may be implemented as described above in FIGS. 1-2. Membership function coefficients and/or constants as described above may be tuned according to classification and/or clustering algorithms. For instance, and without limitation, a clustering algorithm may determine a Gaussian or other distribution of questions about a centroid corresponding to a given compatibility level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 3, an inference engine may be implemented according to input and/or output membership functions and/or linguistic variables. For instance, a first linguistic variable may represent a first measurable value pertaining to plurality of user data, such as a degree of compatibility of an element, while a second membership function may indicate a degree of in plurality of light emission parameters of a subject thereof, or another measurable value pertaining to plurality of user data. Continuing the example, an output linguistic variable may represent, without limitation, a score value. An inference engine may combine rules. The degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T (T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 3, plurality of user data to be used may be selected by user selection, and/or by selection of a distribution of output scores, such as 60% match, 40% moderate match, and 0% no match or the like. Each plurality of light emission parameters categorization may be selected using an additional function such as in plurality of light emission parameters as described above.

Figure 4:
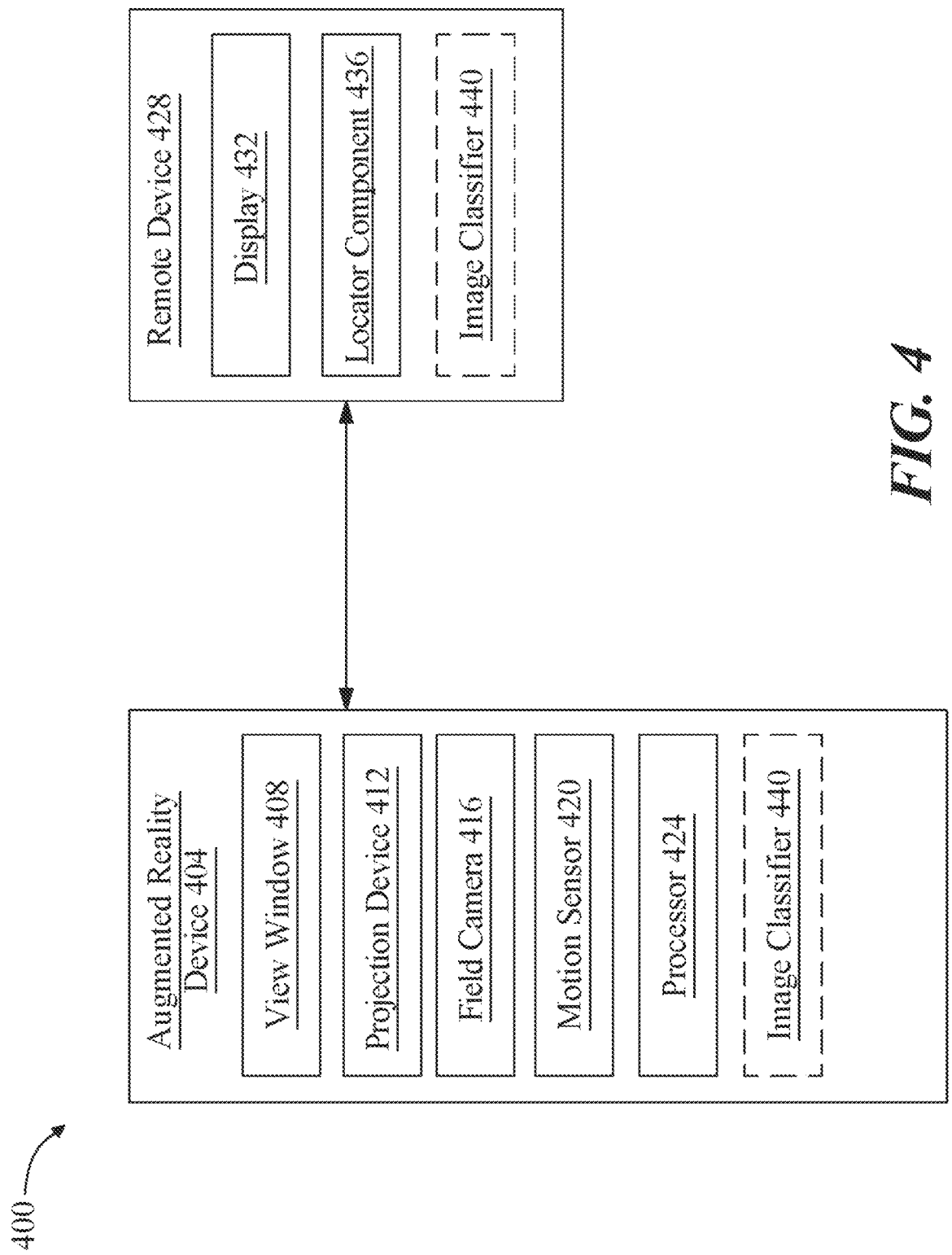
FIG. 4 is a block diagram of exemplary embodiment of an augmented reality device in accordance with one or more embodiments of the present disclosure.

Referring to FIG. 4, an exemplary embodiment of an augmented reality system 400 is illustrated. Augmented reality system may include an Augmented reality device 404 and a remote device 428. Augmented reality device 404 may include a view window 408, defined for the purposes of this disclosure as a portion of the augmented reality device 404 that admits a view of field of vision; view window 408 may include a transparent window, such as a transparent portion of goggles such as lenses or the like. Alternatively, view window 408 may include a screen that displays a field of vision to user. Augmented reality device 404 may include a projection device 412, defined as a device that inserts images into field of vision. Where view window 408 is a screen, projection device 412 may include a software and/or hardware component that adds inserted images into a display 432 signal to be rendered on the display 432. Projection device 412 and/or view window 408 may make use of reflective waveguides, diffractive waveguides, or the like to transmit, project, and/or display 432 images. For instance, and without limitation, projection device 412 and/or display 432 may project images through and/or reflect images off an eyeglass-like structure and/or lens piece, where either both field of vision and images from projection device 412 may be so displayed, or the former may be permitted to pass through a transparent surface. Projection device 412 and/or view window 408 may be incorporated in a contact lens or eye tap device, which may introduce images into light entering an eye to cause display 432 of such images. Projection device 412 and/or view window 408 may display some images using a virtual retina display (VRD)

Referring again to FIG. 4, Augmented reality system 400 may include a remote device 428. Remote device 428 may include any processor and/or computing device containing any processor suitable for use in and/or with augmented reality device 404. Remote device may refer to computing device 120 described in this disclosure. Remote device 428 may include any component and/or element suitable for use with an augmented reality headset. Remote device 428 may be designed and/or configured to perform any method, method step, or sequence of method steps in any embodiment described in this disclosure, in any order and with any degree of repetition. For instance, remote device 428 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Remote device 428 may perform any step or sequence of steps as described in this disclosure in parallel, such as simultaneously and/or substantially simultaneously performing a step two or more times using two or more parallel threads, remote device cores, or the like; division of tasks between parallel threads and/or processes may be performed according to any protocol suitable for division of tasks between iterations. Remote device 428 may be used to wirelessly connect to augmented reality device 404. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing, which may display an image directly on a retina of a user.

Still referring to FIG. 4, remote device 428 may include a display 432. Display 432 may include, without limitation any display 432 as described in this disclosure, including without limitation any display 432 usable with apparatus 400. Remote device 428 may include a locator component 436. A "locator component 436," as used in this disclosure, is a device and/or component that a user can use to point a cursor at a point on a display 432 and/or to draw on an image depicted in the display 432. A locator component 436 may include without limitation a wired or wireless mouse, a touchpad, a touchscreen, a game controller, or the like. A locator component 436 may include a motion-capture device, such as without limitation a device that tracks motion of the user's hands optically and/or using a sensor of motion, which may be implemented in any way suitable for implementation of a motion sensor 420 as described above. Persons skilled in the art, upon reviewing the entirety of this disclosure, will be aware of various ways in which a locator device may be implemented consistently with this disclosure.

Still referring to FIG. 4, augmented reality device 404 and/or remote device 428 may be configured to generate and/or classify images using an image classifier 440. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 120 and/or another device may generate a classifier using a classification algorithm, defined as a processes whereby a computing device 120 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, kernel estimation, learning vector quantization, and/or neural network-based classifiers.

Still referring to FIG. 4, augmented reality device 404 may be implemented in any suitable way, including without limitation incorporation of or in a head mounted display, a head-up display, a display incorporated in eyeglasses, googles, headsets, helmet display systems, or the like, a display incorporated in contact lenses, an eye tap display system including without limitation a laser eye tap device, VRD, or the like. Persons skilled in the art, upon reviewing the entirety of this disclosure, will be aware of various optical projection and/or display technologies that may be incorporated in augmented reality device 404 consistently with this disclosure.

Further referring to FIG. 4, view window 408, projection device 412, and/or other display devices incorporated in augmented reality device 104 may implement a stereoscopic display. A "stereoscopic display," as used in this disclosure, is a display that simulates a user experience of viewing a three-dimensional space and/or object, for instance by simulating and/or replicating different perspectives of a user's two eyes; this is in contrast to a two-dimensional image, in which images presented to each eye are substantially identical, such as may occur when viewing a flat screen display. Stereoscopic display may display two flat images having different perspectives, each to only one eye, which may simulate the appearance of an object or space as seen from the perspective of that eye. Alternatively, or additionally, stereoscopic display may include a three-dimensional display such as a holographic display or the like. Persons skilled in the art, upon reviewing the entirety of this disclosure, will be aware of various alternative or additional types of stereoscopic display 432 that may be employed in augmented reality device 404.

Continuing to refer to FIG. 4, augmented reality device 404 may include a field camera 416. A "field camera 416," as used in this disclosure, is an optical device, or combination of optical devices, configured to capture field of vision as an electrical signal, to form a digital image. Field camera 416 may include a single camera and/or two or more cameras used to capture field of vision; for instance, and without limitation, the two or more cameras may capture two or more perspectives for use in stereoscopic and/or three-dimensional display, as described above. Field camera 416 may capture a feed including a plurality of frames, such as without limitation a video feed.

Referring to FIG. 4, augmented reality device 404 may include at least a motion sensor 420. At least a motion sensor 420 may include, without limitation, a microelectromechanical system (MEMS) sensor. At least a motion sensor 420 may include, without limitation, an inertial measurement unit (IMU). At least a motion sensor 420 may include one or more accelerometers; one or more accelerometers may include a plurality of accelerometers, such as three or more accelerometers positioned to span three dimensions of possible acceleration, so that any direction and magnitude of acceleration in three dimensions may be detected and measured in three dimensions. At least a motion sensor 420 may include one or more gyroscopes; one or more gyroscopes may include a plurality of gyroscopes, such as three or more gyroscopes positioned to span three dimensions of possible acceleration, so that any direction and magnitude of change in angular position in three dimensions may be detected and measured in three dimensions. At least a motion sensor 420 may include, without limitation magnetic sensors such as Hall effect sensors, compasses such as solid-state compasses, or the like. Persons skilled in the art, upon reviewing the entirety of this disclosure, will be aware of various components and/or devices that may be used as at least a motion sensor 420 consistently with this disclosure.

Augmented reality device 404 may include a processor 424. Processor 424 may include and/or be included in any computing device as described in this disclosure, including without limitation a microcontroller, microprocessor, digital signal processor (DSP) and/or system on a chip (SoC) as described in this disclosure. Computing device 120 may include, be included in, and/or communicate with a mobile device such as a mobile telephone or smartphone. Processor 424 may include and/or be included in a single computing device operating independently, or may include two or more computing device operating in concert, in parallel, sequentially or the like; two or more computing devices may be included together in a single computing device or in two or more computing devices. Processor 424 may interface or communicate with one or more additional devices as described below in further detail via a network interface device. Network interface device may be utilized for connecting processor 424 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 424 may include but is not limited to, for example, a computing device or cluster of computing devices in a first location and a second computing device or cluster of computing devices in a second location. Processor 424 may include and/or be included in one or more computing devices dedicated to data storage, security, distribution of traffic for load balancing, and the like. Processor 424 may distribute one or more computing tasks as described below across a plurality of computing devices of computing device, which may operate in parallel, in series, redundantly, or in any other manner used for distribution of tasks or memory between computing devices. Processor 424 may be implemented using a "shared nothing" architecture in which data is cached at the worker, in an embodiment, this may enable scalability of augmented reality device 400 and/or computing device 120.

Still referring to FIG. 4, processor 424 may include a device and/or component incorporated in and/or attached to augmented reality device 404. For instance, processor 424 may include a microcontroller, system on chip, FPGA, or other compact hardware element that is incorporated in and/or attached to augmented reality device 404. Alternatively, or additionally, processor 424 may include a device communicating with augmented reality device 404 via a wireless and/or wired connection. In an embodiment, processor 424 may include a device incorporated in augmented reality device 404 and a device communicating therewith via wired and/or wireless connection.

Processor 424 may be designed and/or configured to perform any method, method step, or sequence of method steps in any embodiment described in this disclosure, in any order and with any degree of repetition. For instance, processor 424 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 424 may perform any step or sequence of steps as described in this disclosure in parallel, such as simultaneously and/or substantially simultaneously performing a step two or more times using two or more parallel threads, processor 424 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Now referring to FIG. 5A-E, exemplary embodiments of one or more templates 500A-E are described. In some cases, template 500A-E may be configured to provide one or more light emission parameters. In some cases, a user may outline a border 504A-E of template 500A-E wherein a computing device may receive predefined boundaries on which to provide photo modification. The predefined boundaries may be received as template datum. In some cases, each template 504A-E may differ in size wherein each size may require differing outputs from a light-emitting device. For example, template 500A may contain a size of 325 square centimeters wherein a boundary drawn around border may indicate that the boundary on a user's skin is 325 square centimeters. In some cases, each template 500A-E may include template parameters 508A-E wherein each template parameter 508A-E may indicate to a user or computing device the desired power output for light emitting device within a given boundary. For example, template 508A may include a template parameter of 325 square centimeters and a total energy output of 32,500 J wherein light emitting device may be configured to provide an energy output through a plurality of pulses or shots. In some cases light emitting device may provide the energy output through a series of pulses wherein each pulse emits 10 joules, and a total of 2300 shots or pulses are emitted over 4 minutes. In some cases, a user may opt to lower the energy output but instead increase the pulses and the length of the photo modification. In some cases template parameters may be received as template datum as described above wherein the template datum may indicate the total power output, the total surface area, the energy per area, the energy per pulse and the like. In some cases, a particular template may be used on differing parts of a patient's body. For example, template 500A may be used on a back of the patient wherein the back of a patient may contain a larger surface area, and template 500C may be used on a leg of the patients wherein the leg of the patient may contain a smaller surface area in comparison to the back. In some cases, template 500A-E may come in differing sizes to satisfy various areas of a patients' body. For example a first template may contain a shape suitable for a patient's face whereas a second template may contain a shape suitable for a patient's back. In some cases, a computing device may be configured to receive the boundaries created by the template and transmit commands to a light emitting device to provide photo modification within the boundaries created by template and provide photo modification based on the template datum present within the template parameters 508A. In some cases, each particular template 500A-E may provide a [articular amount of energy that is to be emitted. In some cases, each particular template 500A-E with a differing energy output may be used to achieve differing outcomes. This may include, but is not limited to, outcomes such as hair removal, photo modification and the like. In some cases, each particular template 500A-E may contain a differing energy output. The energy output may include but is not limited to, 32,500 Joules, 30,000 Joules, 24,500 Joules, 22,500 Joules, 20,000 Joules, 14,400 Joules, 12,500 Joules, 9,000 Joules, 7,000 Joules, 5,000 Joules. In some cases, each template 500A-E may be used to measure out a particular area for photo modification. In some cases, each template 500A-E may be traced on with a stencil, a marker or any other instruments, wherein a device may be guided within the traced boundaries, or along the traced lines. In some cases, each template 500A-E may provide for a particular surface area that is to be guided on.

Figure 6:
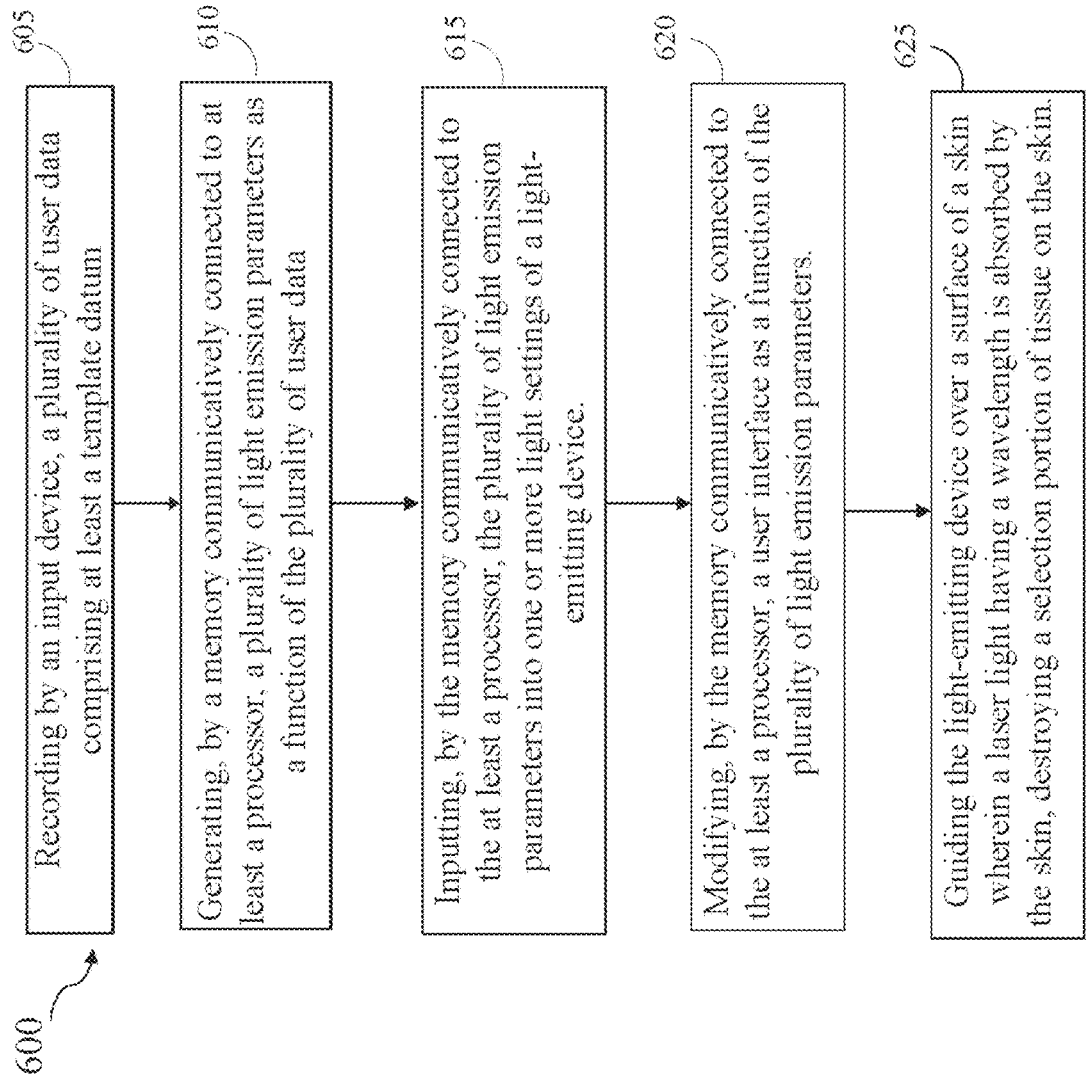
FIG. 6 is a flow diagram of an exemplary method for using a light-emitting device.

Now referring to FIG. 6, an exemplary embodiment of a method 600 for precise tissue photo modification using a light-emitting device 108 is illustrated. At step 605, the method includes recording by an input device, a plurality of user data having at least a template datum. In an embodiment, recording by an input device, a plurality of user data having at least a skin color datum comprises, recording, by at least one video capture device, video data and generating, by the memory communicatively connected to the at least a processor, the plurality of user data as a function of the video data. In some embodiments, the plurality of user data further comprises a hair color datum. In some embodiments, the plurality of user data from the input device further comprising a boundary datum, and the boundary datum defining a predetermined area for a user to guide the laser device. These may be implemented without limitation as described above in reference to FIGS. 1-5.

Still referring to FIG. 6, at step 610 generating, by a memory 128 communicatively connected to a processor 125, a plurality of light emission parameters 150 as a function of the plurality of user data. In some embodiments, generating the plurality of light emission parameters as a function of the function of the skin color datum further comprises, receiving the plurality of user data from the input device, training a light emission learning model as a function of a training datum; and generating the plurality of light emission parameters as a function of the skin color datum and the light emission machine learning model. In some embodiments, method may further comprise determining by a by a memory communicatively connected to the at least a processor, a repetition datum as a function of the plurality of user data, wherein the repetition datum contains a desired number of repetitions for the light-emitting device over a predetermined area of skin of a user. in some embodiments, the method may further comprise, generating, by the memory communicatively connected to the at least a processor, a plurality of body parameters as a function of the plurality of user data. These may be implemented without limitation as described above in reference to FIGS. 1-5.

Still referring to FIG. 6 at step 615, inputting, by the memory communicatively connected to the at least a processor, the plurality of light emission parameters into one or more light settings of a light-emitting device. As described above the one or more settings may include the wavelength settings, pulse width settings and cooling settings of the light-emitting device 108. The light emission parameters may be displayed on a display as described below. The repetition datum displayed may also be displayed onto a display for user. These may be implemented without limitation as described above in reference to FIGS. 1-5.

Still referring to FIG. 6 at step 620, modifying, by the memory communicatively connected to the at least a processor, a user interface as a function of the plurality of light emission parameters. In some embodiments, the method may further comprise generating, by the memory communicatively connected to the processor, a notification to the user when a threshold has been exceeded. In some cases, the notification may be based on and/or dependent on template datum. These may be implemented without limitation as described above in reference to FIGS. 1-5.

Still referring to FIG. 6 at step 625, guiding the light-emitting device over a surface of a skin wherein a laser light having a wavelength is absorbed by the skin, destroying a selected portions of tissue on the skin. In some embodiments, the method may further comprise guiding the light-emitting device over a predetermined area using an automated arm. In some embodiments the method may further comprise displaying by an augmented reality device, an augmented visual filed to a user and wherein modifying, by the memory communicatively connected to the at least a processor, the user interface as a function of the plurality of light emission parameters further comprises, capturing at least an image of a field of vision of the user, generating a visual guide datum as a function of the at least an image and the plurality of light emission parameters, and displaying to the user, an using the augmented reality device, the visual guide datum. These may be implemented without limitation as described above in reference to FIGS. 1-5.

It is to be noted that any one or more of the aspects and embodiments described herein may be conveniently implemented using one or more machines (e.g., one or more computing devices 120 that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 120) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 120 may include and/or be included in a kiosk.

Figure 7:
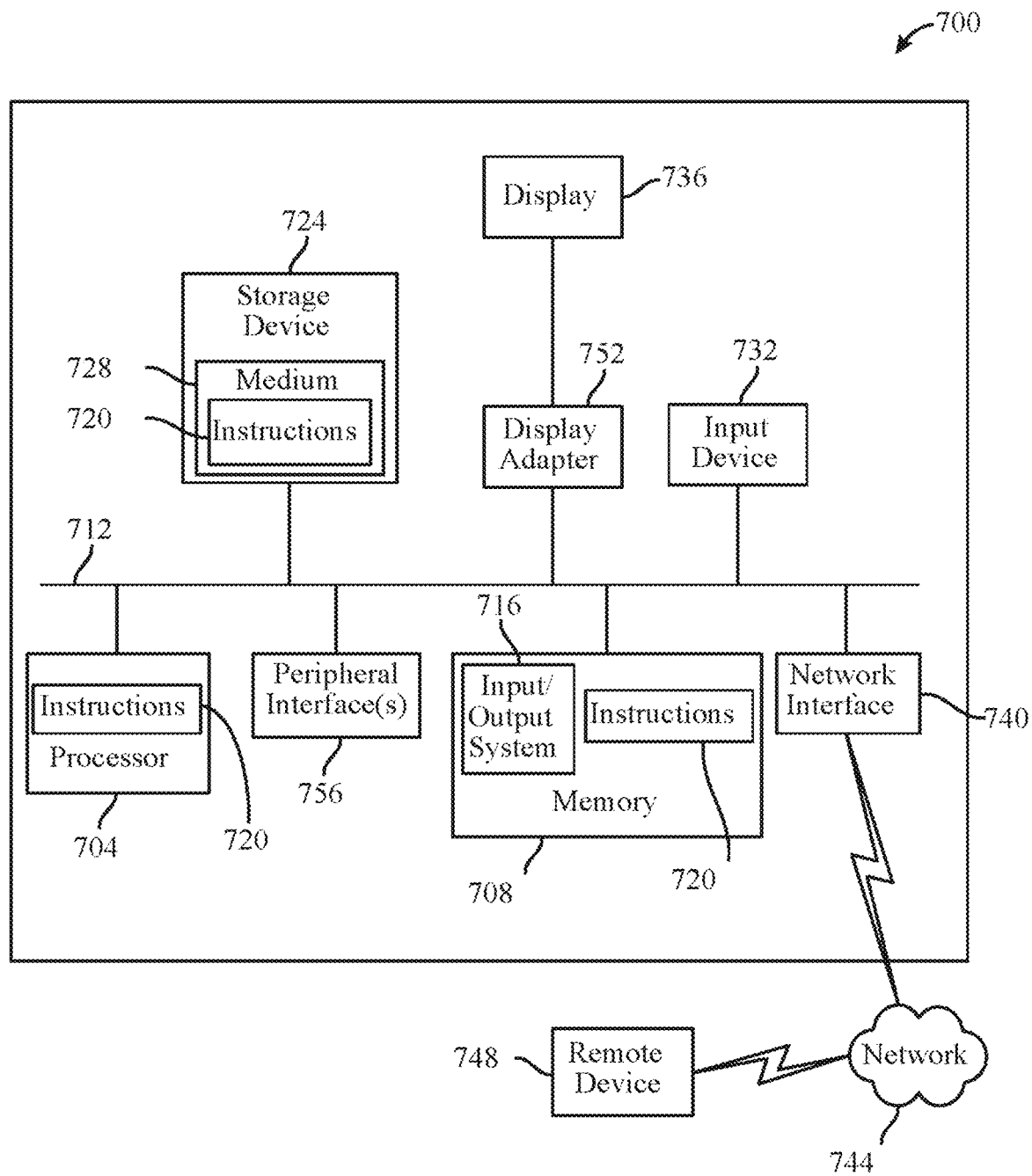
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes the processor 704 and the memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light-emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for precise tissue photo modification, the apparatus comprising:
   at least a template;
   an input device;
   a light-emitting device for use in precise tissue destruction, comprising one or more light settings, the one or more settings having at least a power density setting;
   a processor; and
   a memory communicatively connected to the processor, the memory containing instructions configuring the processor to:
     receive a plurality of user data with respect to a patient from the input device, wherein the plurality of user data comprises at least a template datum;
     generate a plurality of light emission parameters for the one or more light settings as a function of the plurality of the user data and a light emission machine-learning model;
     receive, via a user interface, user feedback with respect to the patient for the plurality of light emission parameters;
     update the plurality of light emission parameters as a function of the user feedback;
     transmit a light command as a function of the updated plurality of light emission parameters;
     generate training data based on the user feedback, wherein the user feedback comprises the plurality of light emission parameters;
     retrain the light emission machine-learning model using the training data; and
     update the plurality of light emission parameters as a function of the user feedback and the retrained light emission machine-learning model.

2. The apparatus of claim 1, wherein the input device includes at least one video capture device, and the memory contains instructions configuring the processor to receive data from the at least one video capture device and generate the plurality of user data.

3. The apparatus of claim 1, wherein the plurality of user data of the input device further comprises a hair color datum.

4. The apparatus of claim 1, wherein:
   the plurality of user data from the input device further comprises a boundary datum; and
   the boundary datum defining a predetermined area for a user to guide the light-emitting device.

5. The apparatus of claim 1, wherein the memory contains instructions configuring the processor to determine a repetition datum as a function of the plurality of user data, wherein the repetition datum contains a desired number of repetitions for the light-emitting device over a predetermined area of skin of a user.

6. The apparatus of claim 1 further comprising a notification system, wherein the notification system is configured to communicate to a user when a threshold has been exceeded.

7. The apparatus of claim 6, wherein the notification system depends on the at least a template datum.

8. The apparatus of claim 1, wherein the memory contains instructions configuring the processor to generate a plurality of body parameters as a function of the plurality of user data.

9. The apparatus of claim 1, further comprising an augmented reality device, the augmented reality device configured to display an augmented visual field to a user, and wherein modifying the user interface comprises:
   capturing at least an image of a field of vision of the user;
   generating a visual guide datum as a function of the at least an image and the plurality of light emission parameters; and
   displaying to the user, using the augmented reality device, the visual guide datum.

10. A method for precise tissue photo modification, the method comprising:
- recording, by an input device, a plurality of user data with respect to a patient comprising at least a template datum;
- generating, by at least a processor, a plurality of light emission parameters as a function of the plurality of user data with respect to a user and a light emission machine-learning model;
- inputting, by the at least a processor, the plurality of light emission parameters into one or more light settings of a light-emitting device;
- receiving, by the at least a processor, via a user interface, user feedback with respect to the patient for the plurality of light emission parameters;
- updating, by the at least a processor, the plurality of light emission parameters as a function of the user feedback;
- transmitting, by the at least a processor, a light command as a function of the updated plurality of light emission parameters;
- guiding the light-emitting device over a surface of a skin wherein a laser light having a wavelength is absorbed by the skin, destroying a selected portion of tissue on the skin; and
- generating, by the processor, training data based on the user feedback, wherein the user feedback comprises the plurality of light emission parameters;
- retraining, by the processor, the light emission machine-learning model using the training data; and
- updating the plurality of light emission parameters as a function of the user feedback and the retrained light emission machine-learning model.

11. The method of claim 10, wherein recording by an input device, a plurality of user data comprises:
- recording, by at least one video capture device, video data; and
- generating, by the at least a processor, the plurality of user data as a function of the video data.

12. The method of claim 10, wherein the plurality of user data of the input device further comprises a hair color datum.

13. The method of claim 10, wherein:
- the plurality of user data from the input device further comprising a boundary datum; and
- the boundary datum defining a predetermined area for a user to guide the light-emitting device.

14. The method of claim 10, the method further comprising determining, by the at least a processor, a repetition datum as a function of the plurality of user data, wherein the repetition datum contains a desired number of repetitions for the light-emitting device over a predetermined area of skin of a user.

15. The method of claim 10, the method further comprising generating, by the at least a processor, a notification to the user when a threshold has been exceeded.

16. The method of claim 15, wherein generating the notification to the user further comprises generating the notification based on the at least a template datum.

17. The method of claim 10, the method further comprising generating, by the at least a processor, a plurality of body parameters as a function of the plurality of user data.

18. The method of claim 10, the method further comprising displaying, by an augmented reality device, an augmented visual field to a user and wherein modifying the user interface as a function of the plurality of light emission parameters comprises:
- capturing at least an image of a field of vision of the user;
- generating a visual guide datum as a function of the at least an image and the plurality of light emission parameters; and
- displaying to the user, using the augmented reality device, the visual guide datum.

* * * * *